US012746079B2

(12) United States Patent
Chandra et al.

(10) Patent No.: US 12,746,079 B2
(45) Date of Patent: Sep. 29, 2026

(54) INCREASING MOBILITY OF COMPUTER-ASSISTED SYSTEMS WHILE MAINTAINING A PARTIALLY CONSTRAINED FIELD OF VIEW

(71) Applicant: INTUITIVE SURGICAL OPERATIONS, INC., Sunnyvale, CA (US)

(72) Inventors: Ramu Sharat Chandra, San Jose, CA (US); Arjang M. Hourtash, Millbrae, CA (US); Jordan M. Klein, Palo Alto, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 19/118,730

(22) PCT Filed: Oct. 3, 2023

(86) PCT No.: PCT/US2023/034401

§ 371 (c)(1),
(2) Date: Apr. 4, 2025

(87) PCT Pub. No.: WO2024/076592

PCT Pub. Date: Apr. 11, 2024

(65) Prior Publication Data

US 2026/0130728 A1 May 14, 2026

Related U.S. Application Data

(60) Provisional application No. 63/413,041, filed on Oct. 4, 2022.

(51) Int. Cl.

| | |
|---|---|
| ***A61B 34/30*** | (2016.01) |
| ***A61B 34/32*** | (2016.01) |
| ***A61B 34/35*** | (2016.01) |

(52) U.S. Cl.
CPC .............. *A61B 34/32* (2016.02); *A61B 34/35* (2016.02); *A61B 2034/301* (2016.02)

(58) Field of Classification Search
USPC .............................. 700/245–264; 606/1, 130
See application file for complete search history.

(56) References Cited

U.S. PATENT DOCUMENTS 6,789,755 B1 * 9/2004 Mack ...................... A01K 1/01 239/587.5
8,620,473 B2 12/2013 Diolaiti et al.
(Continued)

FOREIGN PATENT DOCUMENTS

WO WO-2013071057 A1 5/2013
WO WO-2013071071 A1 5/2013
(Continued)

OTHER PUBLICATIONS

International Search Report and Written Opinion for Application No. PCT/US2023/034401, mailed Jan. 19, 2024, 14 pages.
(Continued)

*Primary Examiner* — Jonathan L Sample
(74) *Attorney, Agent, or Firm* — Artegis Law Group, LLP

(57) ABSTRACT

A system includes proximal and distal structures and a processor system. The processor system determines a first commanded motion of the proximal structure; determine a second commanded motion for joint(s) of the distal structure or an imaging device, wherein when the first and second commanded motions are performed in conjunction, a field of view of the imaging device is maintained relative to a workspace; and in response to determining that driving the joint(s) in accordance with the second commanded motion would cause the distal structure or the imaging device to violate a constraint: determines an alternate commanded motion for the joint(s) to maintain a defined geometric relationship between a first geometric feature fixed relative
(Continued)

to the imaging device and a second geometric feature fixed relative to the workspace, drives the proximal structure in accordance with the first commanded motion, and drives the joint(s) in accordance with the alternate commanded motion.

22 Claims, 10 Drawing Sheets

(56) References Cited

U.S. PATENT DOCUMENTS

| | | | | |
|---|---|---|---|---|
| 8,903,546 | B2 | 12/2014 | Diolaiti et al. | |
| 9,084,623 | B2 | 7/2015 | Gomez et al. | |
| 9,138,129 | B2 | 9/2015 | Diolaiti | |
| 9,586,323 | B2 | 3/2017 | Diolaiti et al. | |
| 10,575,908 | B2 * | 3/2020 | Schena | A61B 34/30 |
| 10,959,783 | B2 * | 3/2021 | Gregerson | A61B 34/20 |
| 11,166,770 | B2 * | 11/2021 | DiMaio | B25J 9/1664 |
| 2005/0154431 | A1 * | 7/2005 | Quistgaard | A61B 5/6843 607/96 |
| 2006/0149418 | A1 * | 7/2006 | Anvari | A61B 34/74 700/245 |
| 2008/0161830 | A1 * | 7/2008 | Sutherland | A61B 34/74 606/130 |
| 2009/0062604 | A1 | 3/2009 | Minosawa et al. | |
| 2009/0192524 | A1 * | 7/2009 | Itkowitz | B25J 9/1689 606/130 |
| 2012/0290134 | A1 * | 11/2012 | Zhao | B25J 9/1689 901/47 |
| 2013/0325031 | A1 * | 12/2013 | Schena | A61B 34/37 606/130 |
| 2014/0055489 | A1 * | 2/2014 | Itkowitz | A61B 34/37 345/633 |
| 2015/0100066 | A1 * | 4/2015 | Kostrzewski | A61B 34/30 606/130 |
| 2015/0327940 | A1 | 11/2015 | Inoue et al. | |
| 2016/0135816 | A1 * | 5/2016 | Lavallee | A61B 17/154 606/88 |
| 2016/0157942 | A1 * | 6/2016 | Gombert | A61B 34/30 606/130 |
| 2016/0184032 | A1 * | 6/2016 | Romo | A61B 34/30 901/46 |
| 2016/0199142 | A1 * | 7/2016 | Griffiths | A61B 34/37 606/130 |
| 2017/0000574 | A1 * | 1/2017 | Itkowitz | B25J 9/1689 |
| 2019/0216555 | A1 * | 7/2019 | DiMaio | A61B 90/50 |
| 2019/0380798 | A1 * | 12/2019 | Itkowitz | A61B 34/74 |
| 2022/0022980 | A1 * | 1/2022 | DiMaio | A61B 90/50 |

FOREIGN PATENT DOCUMENTS

| | | | |
|---|---|---|---|
| WO | WO-2018165320 | A1 | 9/2018 |
| WO | WO-2021061105 | A1 | 4/2021 |
| WO | WO-2022046787 | A1 | 3/2022 |

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.
International Preliminary Report on Patentability for Application No. PCT/US2023/034401, mailed Apr. 17, 2025, 9 pages.

* cited by examiner

INCREASING MOBILITY OF COMPUTER-ASSISTED SYSTEMS WHILE MAINTAINING A PARTIALLY CONSTRAINED FIELD OF VIEW

RELATED APPLICATIONS

This application is a U.S. National Stage patent application of International Patent Application No. PCT/US2023/034401, filed Oct. 3, 2023, and claims the benefit of U.S. Provisional Application No. 63/413,041, filed Oct. 4, 2022, and entitled "Increasing Mobility of Computer-assisted Systems while Maintaining a Partially Constrained Field of View," the subject matter of these related applications is incorporated by reference herein.

TECHNICAL FIELD

The present disclosure relates generally to computer-assisted systems and more particularly to increasing mobility of computer-assisted systems while maintaining a partially constrained field of view.

BACKGROUND

Some computer-assisted systems include one or more instruments that are repositioned in order to perform various procedures. The computer-assisted system can be automated, semi-automated, teleoperated, etc. In a teleoperated example, a human operator manipulates one or more leader input controls to command motion of one or more follower instruments located in a workspace. In some examples, the teleoperated system is configured to support an instrument that includes an imaging device, such as a camera, that enables the operator to observe the workspace. In some instances, the field of view of the imaging device is directed to enable the operator to see other instrument(s) as the operator commands motion of the instrument(s).

In some examples, a proximal repositionable structure is located proximal to one or multiple distal repositionable structures. In a multiple distal repositionable structure example, a first distal repositionable structure is configured to support a first instrument comprising the imaging device, and a second distal repositionable structure is configured to support a second instrument. In operation, movement of the proximal repositionable structure can be used to produce motion of the first and/or second distal repositionable structures. Thus, in operation, movement of the proximal repositionable structure can be used to produce motion that moves, or assists in the movement of, the imaging device supported by the first distal repositionable structure or one or more second instruments supported by the second distal repositionable structure. Where the proximal repositionable structure moves, the motion of the proximal repositionable structure can also move the first distal repositionable structure supporting an imaging device, and thus motion of the proximal repositionable structure can also move a field of view of the imaging device. To maintain an orientation, a position, or both an orientation and a position, of the field of view of the imaging device, the computer-assisted system can command movement of one or more joints of the imaging device and/or the first distal repositionable structure while commanding movement of the proximal repositionable structure.

However, in cases where the one or more joints of the imaging device cannot fully compensate for the movement of the proximal repositionable structure, the computer-assisted system can no longer maintain the field of view while moving the proximal repositionable structure. As a result, performing the operator commanded motion of the one or more second instruments results in movement of the field of view of the imaging device. Such movement of the field of view can be unexpected and/or disconcerting to the operator of the computer-assisted system, and the like.

Accordingly, improved techniques for controlling movement of repositionable structures with less uncommanded movement of the field of view are desirable.

SUMMARY

Consistent with some embodiments, a computer-assisted system, and method implemented therein, includes a computer-assisted system comprising: a proximal repositionable structure; a first distal repositionable structure physically coupled to the proximal repositionable structure; and a processor system communicatively coupled to the proximal repositionable structure, and the first distal repositionable structure. The processor system is configured to determine a first commanded motion of the proximal repositionable structure. The processor system is further configured to determine a second commanded motion for one or more joints, the one or more joints selected from the group consisting of: joints of the first distal repositionable structure and an imaging device supported by the first distal repositionable structure, wherein when the second commanded motion is performed in conjunction with the first commanded motion, a field of view of the imaging device is maintained relative to a workspace. The processor system is further configured to determine whether driving the one or more joints in accordance with the second commanded motion would cause the first distal repositionable structure or the imaging device to violate a first constraint. The processor system is further configured to, in response to a determination that driving the one or more joints in accordance with the second commanded motion would cause the first distal repositionable structure or the imaging device to violate the first constraint: determine an alternate second commanded motion for the one or more joints to maintain a defined geometric relationship between a first geometric feature and a second geometric feature, the first geometric feature fixed relative to the imaging device, and the second geometric feature fixed relative to the workspace, drive the proximal repositionable structure in accordance with the first commanded motion, and drive the one or more joints in accordance with the alternate second commanded motion.

Consistent with some embodiments, a method includes determining, by a processor system, a first commanded motion of a proximal repositionable structure. The method further includes determining, by the processor system, a second commanded motion for one or more joints, the one or more joints selected from the group consisting of: joints of a first distal repositionable structure and an imaging device supported by the first distal repositionable structure, wherein when the second commanded motion is performed in conjunction with the first commanded motion, a field of view of the imaging device is maintained relative to a workspace. The method further includes determining, by the processor system, whether driving the one or more joints in accordance with the second commanded motion would cause the first distal repositionable structure or the imaging device to violate a first constraint. The method further includes, in response to a determination that driving the one or more joints in accordance with the second commanded motion would cause the first distal repositionable structure or the imaging device to violate the first constraint: determining, by the processor system, an alternate second commanded motion for the one or more joints to maintain a defined geometric relationship between a first geometric feature and a second geometric feature, the first geometric feature fixed relative to the imaging device, and the second geometric feature fixed relative to the workspace, driving, by the processor system, the proximal repositionable structure in accordance with the first commanded motion, and driving, by the processor system, the one or more joints in accordance with the alternate second commanded motion.

Consistent with some embodiments, one or more non-transitory machine-readable media include a plurality of machine-readable instructions which when executed by a processor system are adapted to cause the processor system to perform any of the methods described herein.

Figure 1:
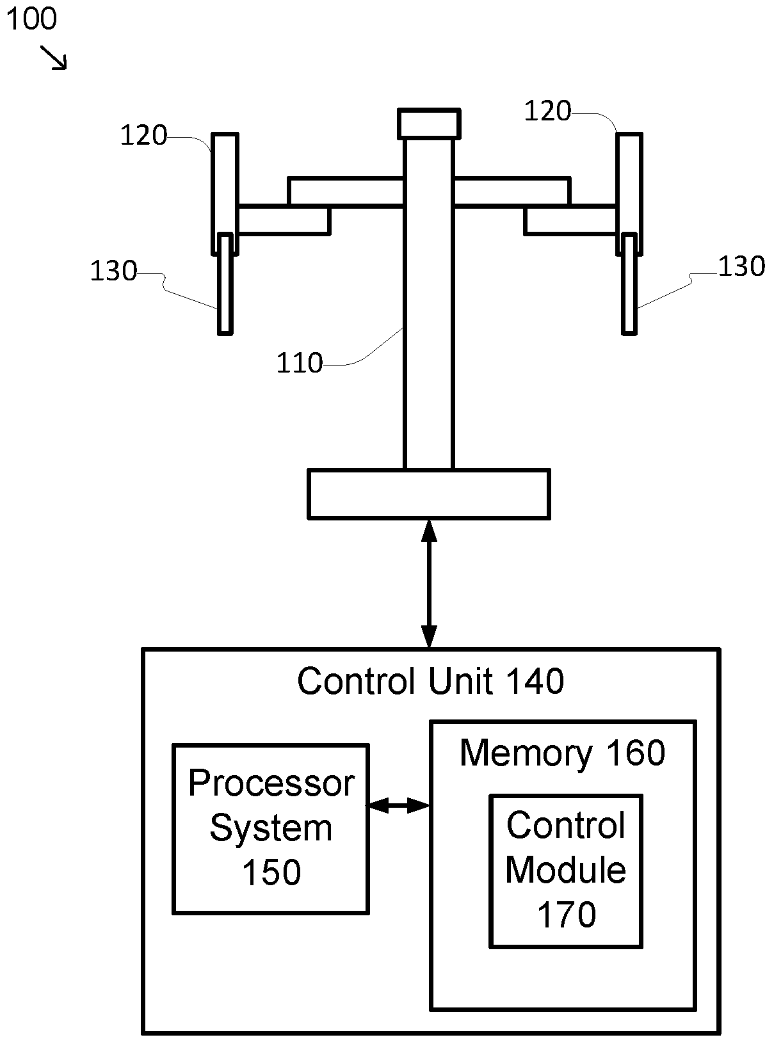
FIG. 1 is a diagram of a computer-assisted system in accordance with one or more embodiments.

In the figures, elements having the same designations have the same or similar functions.

DETAILED DESCRIPTION

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, the terminology in this description is not intended to limit the invention. For example, spatially relative terms—such as "beneath", "below", "lower", "above", "upper", "proximal", "distal", and the like—may be used to describe the relation of one element or feature to another element or feature as illustrated in the figures. These spatially relative terms are intended to encompass different positions (i.e., locations) and orientations (i.e., rotational placements) of the elements or their operation in addition to the position and orientation shown in the figures. For example, if the content of one of the figures is turned over, elements described as "below" or "beneath" other elements or features would then be "above" or "over" the other elements or features. A device may be otherwise oriented and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or module may, whenever practical, be included in other embodiments, implementations, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances, well known methods, procedures, components, and circuits have not been described in detail so as not to unnecessarily obscure aspects of the embodiments.

This disclosure describes various devices, elements, and portions of computer-assisted systems and elements in terms of their state in three-dimensional space. As used herein, the term "position" refers to the location of an element or a portion of an element (e.g., three degrees of translational freedom in a three-dimensional space, such as along Cartesian x-, y-, and z-coordinates). As used herein, the term "orientation" refers to the rotational placement of an element or a portion of an element (e.g., three degrees of rotational freedom in three-dimensional space, such as about roll, pitch, and yaw axes, represented in angle-axis, rotation matrix, quaternion representation, and/or the like). As used herein, and for a device with a kinematic series, such as with a repositionable structure with a plurality of links coupled by one or more joints, the term "proximal" refers to a direction toward a base of the kinematic series, and "distal" refers to a direction away from the base along the kinematic series.

As used herein, the term "pose" refers to the multi-degree of freedom (DOF) spatial position and orientation of a coordinate system of interest attached to a rigid body. In general, a pose includes a pose variable for each of the DOFs in the pose. For example, a full 6-DOF pose for a rigid body in three-dimensional space would include 6 pose variables corresponding to the 3 positional DOFs (e.g., x, y, and z) and the 3 orientational DOFs (e.g., roll, pitch, and yaw). A 3-DOF position only pose would include only pose variables for the 3 positional DOFs. Similarly, a 3-DOF orientation only pose would include only pose variables for the 3 rotational DOFs. Further, a velocity of the pose captures the change in pose over time (e.g., a first derivative of the pose). For a full 6-DOF pose of a rigid body in three-dimensional space, the velocity would include 3 translational velocities and 3 rotational velocities. Poses with other numbers of DOFs would have a corresponding number of velocities translational and/or rotational velocities.

Aspects of this disclosure are described in reference to computer-assisted systems, which can include devices that are teleoperated, externally manipulated, autonomous, semi-autonomous, and/or the like. Further, aspects of this disclosure are described in terms of an implementation using a teleoperated surgical system, such as the da Vinci® Surgical System commercialized by Intuitive Surgical, Inc. of Sunnyvale, California. Knowledgeable persons will understand, however, that inventive aspects disclosed herein may be embodied and implemented in various ways, including teleoperated and non-teleoperated, and medical and non-medical embodiments and implementations. Implementations on da Vinci® Surgical Systems are merely exemplary and are not to be considered as limiting the scope of the inventive aspects disclosed herein. For example, techniques described with reference to surgical instruments and surgical methods may be used in other contexts. Thus, the instruments, systems, and methods described herein may be used for humans, animals, portions of human or animal anatomy, industrial systems, general robotic, or teleoperated systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (with or without return to a human or animal anatomy) and for procedures on human or animal cadavers. Further, these techniques can also be used for medical treatment or diagnosis procedures that include, or do not include, surgical aspects.

FIG. 1 is a diagram of a computer-assisted system 100 in accordance with one or more embodiments. As shown in FIG. 1, the computer-assisted system 100 includes a manipulating assembly 110 with one or more repositionable structures 120. In the example of FIG. 1, the repositionable structure(s) are shown as manipulator arms comprising a plurality of links coupled by one or more joints. Each of the one or more repositionable structures 120 supports one or more instruments 130. In some examples, the manipulating assembly 110 comprises a computer-assisted surgical assembly. Examples of medical instruments include surgical instruments for interacting with tissue, imaging, sensing devices, and/or the like. In some examples, the instruments 130 can include end effectors that are capable of, but are not limited to, performing, gripping, retracting, cauterizing, ablating, suturing, cutting, stapling, fusing, sealing, etc., and/or combinations thereof.

In a teleoperation example, the manipulating assembly 110 can further be communicatively coupled by wired or wireless connection to a user input system (not shown). The user input system includes one or more input controls, also referred to herein as input controls, for operating the manipulating assembly 110, the one or more repositionable structures 120, and/or the instruments 130. In some examples, the one or more input controls can include kinematic series of links and one or more joint(s), one or more actuators for driving portions of the input control(s), robotic manipulators, levers, pedals, switches, keys, knobs, triggers, and/or the like. In some examples, the one or more input controls comprise a leader device (also called a "master" device in industry), and the manipulating assembly 110 and/or the one or more repositionable structures 120 (either supporting or not supporting instruments 130) comprise a follower device (also called a "slave" device in industry). An operator can use the one or more input controls to command motion of the manipulating assembly 110, such as by commanding motion of the one or more repositionable structures 120 and/or instruments 130, in a leader-follower configuration. The leader-follower configuration is a type of teleoperation configuration, and is sometimes called a master-slave configuration in industry.

In examples supporting external manipulation, the input controls can be located at the repositionable structure. As a specific example, the input controls can comprise joint sensors that detect joint deflection, and the computer-assisted system is configured to process certain joint deflections to be commands to move the joint.

The manipulating assembly 110 of FIG. 1 is coupled to a control unit 140 via an interface. The interface can be wired and/or wireless, and can include one or more cables, fibers, connectors, and/or buses and can further include one or more networks with one or more network switching and/or routing devices. Operation of the control unit 140 is controlled by a processor system 150. Processor system 150 can include one or more central processing units, multi-core processors, microprocessors, microcontrollers, digital signal processors, field programmable gate arrays (FPGAs), application specific integrated circuits (ASICs), graphics processing units (GPUs), tensor processing units (TPUs), and/or the like in the control unit 140. The control unit 140 can be implemented as a stand-alone subsystem and/or board added to a computing device or as a virtual machine. In some embodiments, the control unit 140 can be included as part of the user input system and/or the manipulating assembly 110, and/or be operated separately from, and in coordination with, the user input system and/or the manipulating assembly 110.

As one example, the manipulating assembly 110, the user input system, and/or the control unit 140 can correspond to the patient side cart, the surgeon console, and the processing units and associated software of da Vinci® Surgical System commercialized by Intuitive Surgical, Inc. of Sunnyvale, California. In some embodiments, manipulating assemblies with other configurations, such as fewer or more repositionable structures, different user input systems or input controls, different repositionable structure hardware, and/or the like, can comprise the computer-assisted system 100.

The memory 160 can be used to store software executed by the control unit 140 and/or one or more data structures used during operation of the control unit 140. The memory 160 can include one or more types of machine-readable media. Some common forms of machine-readable media can include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip, or cartridge, and/or any other medium from which a processor or computer is adapted to read.

As shown in the example of FIG. 1, the memory 160 includes a control module 170 that can be used to support autonomous, semiautonomous, and/or teleoperated control of the manipulating assembly 110. The control module 170 includes one or more application programming interfaces (APIs) for receiving position, motion, force, torque, and/or other sensor information from the manipulating assembly 110, the repositionable structures 120, and/or the instruments 130, for sharing position, motion, force, torque, and/or collision avoidance information with other control units regarding other devices, and/or planning and/or assisting in the planning of motion for the manipulating assembly 110 (such as motion of the repositionable structures 120), and/or the instruments 130. In some examples, the control module 170 further supports autonomous, semiautonomous, and/or teleoperated control of the manipulating assembly 110 and/or the instruments 130 during the performance of various tasks. And although the control module 170 is depicted as a software application, the control module 170 can optionally be implemented using hardware, software, and/or a combination of hardware and software.

In some medical embodiments, the computer-assisted system 100 can be found in a clinic, diagnostic facility, an operating room, an interventional suite, or other medical environment. Although the computer-assisted system 100 is shown comprising one manipulating assembly 110 with two repositionable structures 120, each supporting a corresponding instrument 130, one of ordinary skill would understand that the computer-assisted system 100 can include any number of manipulating assemblies, each manipulating assembly can comprise one or more repositionable structures, and each repositionable structure can support one or more instruments, and that all of these elements may be similar or different in design from that specifically depicted in these figures. In some examples, each of the manipulating assemblies can include fewer or more repositionable structures, and/or support fewer or more instruments, than specifically depicted in these figures.

Figure 2:
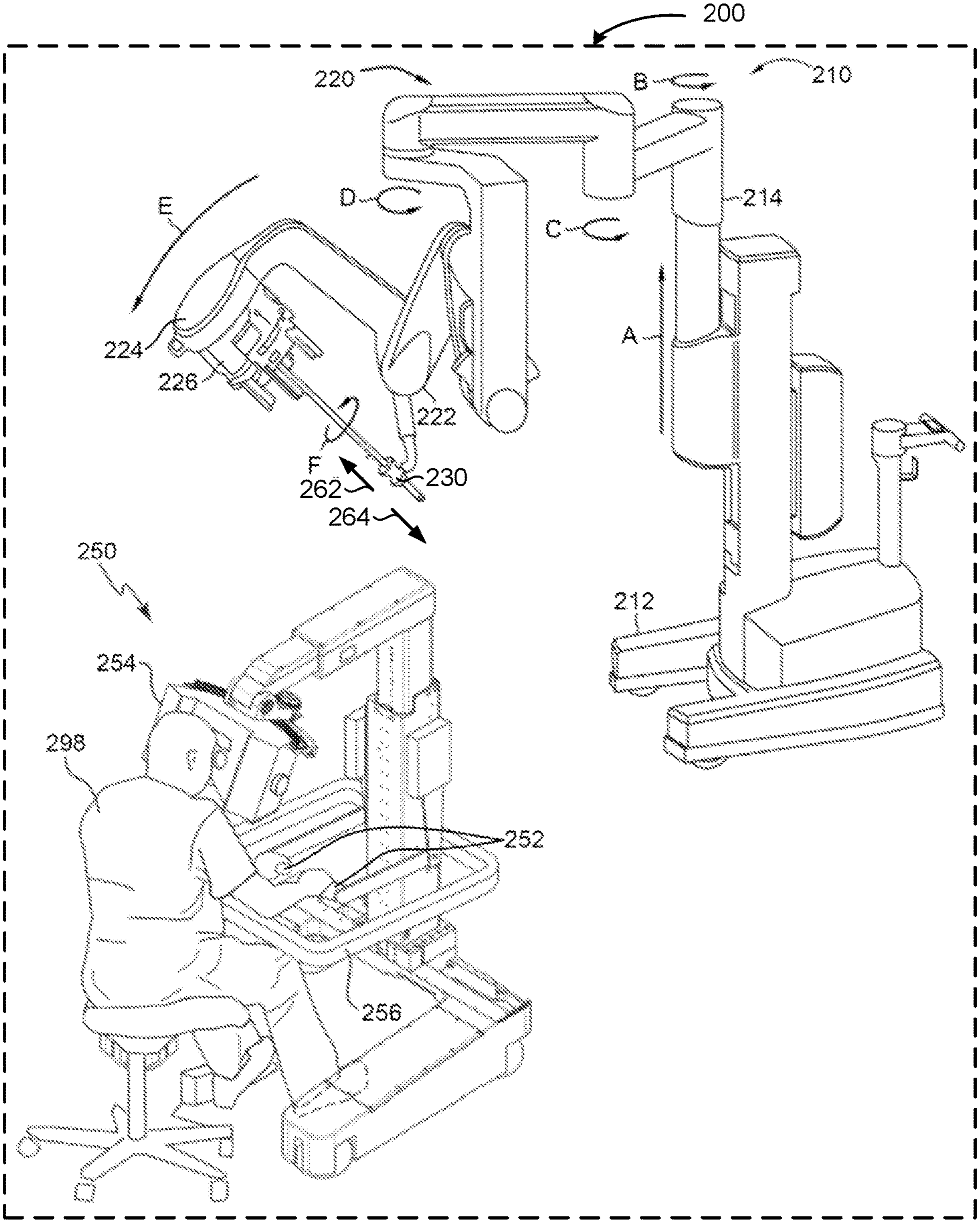
FIG. 2 is a diagram of a computer-assisted system in accordance with one or more embodiments.

FIG. 2 is a diagram of a computer-assisted system 200 in accordance with one or more embodiments. The computer-assisted system 200, in the example of FIG. 2, includes a repositionable structure shown as a manipulating assembly 210, and a user input system 250. In a teleoperation scenario, an operator 298 uses the user input system 250 to operate the manipulating assembly 210, such as in a leader-follower configuration. In the leader-follower configuration for the example of FIG. 1, a component of the user input system 250 (e.g., an input control) is the leader, and a portion of the manipulating assembly 210 (e.g., a manipulator arm or other repositionable structure) is the follower.

The manipulating assembly 210 can be used to introduce a set of instruments into a work site through a single port 230 (e.g., using a cannula as shown) inserted in an aperture. In a medical scenario, the work site can be on or within a body of a patient, and the aperture can be a minimally invasive incision or a natural body orifice. The port 230 can be free-floating, held in place by a fixture separate from the manipulating assembly 210, or held by a linkage 222 or other part of the manipulating assembly 210. The linkage 222 can be coupled to additional joints and links 214, 220 of the manipulating assembly 210, and these additional joints and links 214, 220 can be mounted on a base 212. The linkage 222 can further include a manipulator-supporting link 224 located in a proximal direction 262 to the port 230. A set of manipulators 226 located in the proximal direction 262 to the port 230 can couple to the manipulator-supporting link 224. The repositionable structure that can be moved to follow commands from the user input system 250 can include one or more of any of the following: the linkage 222, additional joints and links 214, 220, base 212, manipulator-supporting link 224, and/or any additional links or joints coupled to the foregoing joints or links. Each of the manipulators 226 can include a carriage (or other instrument-coupling link) configured to couple to an instrument, and each of the manipulators 226 can include one or more joint(s) and/or link(s) that can be driven to move the carriage. For example, a manipulator 226 can include a prismatic joint that, when driven, linearly moves the carriage and any instrument(s) coupled to the carriage. This linear motion can be along (parallel to) an insertion axis that extends in a distal direction 264 to and through port 230.

The additional joints and additional links 214, 220 can be used to position the port 230 at the aperture or another position. FIG. 2 shows a prismatic joint for vertical adjustment (as indicated by arrow "A") and a set of rotary joints for horizontal adjustment (as indicated by arrows "B" and "C") that can be used to translate a position of the port 230. The linkage 222 is used to pivot the port 230 (and the instruments disposed within the port at the time) in yaw, pitch, and roll angular rotations about a remote center of motion (RCM) located in proximity to port 230 as indicated by arrows D, E, and F, respectively, without translating the RCM.

Actuation of the degrees of freedom provided by joint(s) of the instrument(s) (not shown) can be provided by actuators disposed in, or whose motive force (e.g., linear force or rotary torque) is transmitted to, the instrument(s). Examples of actuators include rotary motors, linear motors, solenoids, and/or the like. The actuators can drive transmission elements in the manipulating assembly 210 and/or in the instruments to control the degrees of freedom of the instrument(s). For example, the actuators can drive rotary discs of the manipulator that couple with drive elements (e.g., rotary discs, linear slides) of the instrument(s), where driving the driving elements of the instruments drives transmission elements in the instrument that couple to move the joint(s) of the instrument, or to actuate some other function of the instrument, such as a degree of freedom of an end effector. Accordingly, the degrees of freedom of the instrument(s) can be controlled by actuators that drive the instrument(s) in accordance with control signals. The control signals can be determined to cause instrument motion or other actuation as determined automatically by the system, as indicated to be commanded by movement or other manipulation of the input controls, or any other control signal. Furthermore, appropriately positioned sensors, e.g., encoders, potentiometers, and/or the like, can be provided to enable measurement of indications of the joint positions, or other data that can be used to derive joint position, such as joint velocity. The actuators and sensors can be disposed in, or transmit to or receive signals from, the manipulator(s) 226. Techniques for manipulating multiple instruments in a computer-assisted system are described more fully in Patent Cooperation Treaty Patent Application No. PCT/US2021/047374, filed Aug. 24, 2021, and entitled "METHOD AND SYSTEM FOR COORDINATED MULTIPLE-TOOL MOVEMENT USING A DRIVABLE ASSEMBLY," which is incorporated herein by reference.

While a particular configuration of the manipulating assembly 210 is shown in FIG. 2, those skilled in the art will appreciate that embodiments of this disclosure can be used with any design of manipulating assembly or other repositionable structure. In some examples, a manipulating assembly can have any number and any types of degrees of freedom, can be configured to couple or not couple to an entry port, can optionally use a port other than a cannula, such as a guide tube, and/or the like. In some examples, the manipulating assembly 210 can also include an arrangement of links and joints that does not provide a remote center of motion.

In the example shown in FIG. 2, the user input system 250 includes one or more input controls 252 configured to be operated by the operator 298. In the example shown in FIG. 2, the one or more input controls 252 are contacted and manipulated by the hands of the operator 298, with one input control 252 for each hand. Examples of such hand-input-devices include any type of device manually operable by human user, e.g., joysticks, trackballs, button clusters, and/or other types of haptic devices typically equipped with multiple degrees of freedom. Position, force, and/or tactile feedback devices (not shown) can be employed to transmit position, force, and/or tactile sensations from the instruments back to the hands of the operator 298 through the input controls 252.

The input controls 252 are supported by the user input system 250 and are shown as mechanically grounded, and in other implementations can be mechanically ungrounded. An ergonomic support 256 can be provided in some implementations; for example, FIG. 2 shows an ergonomic support 256 including forearm rests on which the operator 298 can rest his or her forearms while manipulating the input controls 252. In some examples, the operator 298 can perform tasks at a work site near the manipulating assembly 210 during a procedure by controlling the manipulating assembly 210 using the input controls 252.

A display unit 254 is included in the user input system 250. The display unit 254 can display images for viewing by the operator 298. The display unit 254 can provide the operator 298 with a view of the worksite with which the manipulating assembly 210 interacts. The view can include stereoscopic images or three-dimensional images to provide a depth perception of the worksite and the instrument(s) of the manipulating assembly 210 in the worksite. The display unit 254 can be moved in various degrees of freedom to accommodate the viewing position of the operator 298 and/or to provide control functions. Where a display unit (such as the display unit 254 is also used to provide control functions, such as to command the manipulating assembly 210, the display unit also includes an input control (e.g., another input control 252).

When using the user input system 250, the operator 298 can sit in a chair or other support, position his or her eyes to see images displayed by the display unit 254, grasp and manipulate the input controls 252, and rest his or her forearms on the ergonomic support 256 as desired. In some implementations, the operator 298 can stand at the station or assume other poses, and the display unit 254 and input controls 252 can differ in construction, be adjusted in position (height, depth, etc.), and/or the like.

In some examples, the repositionable structure includes a base manipulator and multiple instrument manipulators coupled to the base manipulator. In some examples, the repositionable structure includes a single instrument manipulator and no serial coupling of manipulators. In some examples, the repositionable structure includes a single instrument manipulator coupled to a single base manipulator. In some examples, the computer-assisted system can include a moveable-base that is cart-mounted or mounted to an operating table, and one or more manipulators mounted to the moveable base.

In many of the examples described in this application, the repositionable structure includes one or more proximal repositionable structures and one or more distal repositionable structures. In some examples, the one or more proximal repositionable structures can include one or more of any of the linkage 222, additional joints and/or links 214, 220, manipulator-supporting link 224, and/or any additional links and/or joints coupled to the foregoing joints or links. The one or more distal repositionable structures can include one or more of the manipulators 226, carriages (or other instrument-coupling links) configured to couple to instruments, and/or one or more joint(s) and/or link(s) that can be driven to move the carriages. The operator 298 views the workspace via an imaging device coupled to one or more distal repositionable structure(s) in the form of one of the manipulators 226 and associated carriages, joints, and/or links. The imaging device has a field of view that can be displayed on the display unit 254. The operator 298 contacts and manipulates the one or more input controls 252 to generate commanded motions to move the repositionable structure. In response, one or more corresponding distal repositionable structures move in order to move the instruments according to the commanded motion.

The workspace may or may not move relative to the larger environment containing the workspace during a procedure. In various instances, the workspace may be fixed in position and/or orientation relative to the larger environment containing the workspace, for the duration of the procedure. For example, a work piece containing or otherwise defining the workspace may be rigid and may be located at a same location and orientation on a platform; further, the platform may not move in the physical environment containing the platform during the procedure. In various instances, the workspace may translate and/or rotate, during a procedure, relative to the larger environment containing the workspace. For example, a work piece containing or otherwise defining the workspace may be compliant, and physically reconfigure at one or more time during the procedure. As another example, a work piece containing or otherwise defining the workspace may autonomously move, or be externally manipulated to move, relative to the physical environment containing the platform the during the procedure. In a medical example, a patient in which a procedure is performed may change shape or orientation due to breathing or other autonomous movements, may be moved by medical personnel, or be moved by movement of a table on which the patient rests.

In some cases, the corresponding distal repositionable structures can be subject to certain constraints, such that these distal repositionable structures cannot be moved according to the commanded motion. As described herein, the constraint can be a physical constraint, such as a mechanical limit on a position of a repositionable structure and/or an instrument supported by the repositionable structure. In some instances, such a mechanical limit is imposed by the physical design or construction of the repositionable structure and/or the instrument. In some instances, such a mechanical limit is imposed by physical objects in the operating environment of the repositionable structure and/or the instrument. Example physical objects include people, equipment, walls and floors, etc. The constraint can be a motion constraint, where a repositionable structure and/or an instrument is limited in one or more motion parameters such as position, velocity, speed, and/or acceleration. In some instances, such a mechanical limit is imposed by the physical design or construction of the repositionable structure and/or the instrument, such as by any actuators or transmission components of these objects. In some instances, such a mechanical limit is imposed by other operational considerations such as reducing the likelihood of collision or damage, reducing power consumption, reducing vibration, increasing the accuracy of motion, and the like.

In such cases where a distal repositionable structure cannot be moved according to the commanded motion, one or more of the proximal repositionable structures can be moved instead of or in addition to these distal repositionable structures, such that the combined movement of the proximal repositionable structure(s) and the distal repositionable structure(s) moves the instrument according to the commanded motions. The movement of the proximal repositionable structure(s) can also result in the movement of the distal repositionable structure(s) coupled to the imaging device. As a result, the field of view of the imaging device also moves, which can be disorienting or unintuitive to the operator 298. Therefore, the distal repositionable structure(s) coupled to the imaging device move in a manner so as to maintain the field of view of the imaging device.

Under certain circumstances, one or more of the joints of the distal repositionable structure(s) coupled to the imaging device could be commanded to maintain a field of view of an imaging device, but the one or more joints of one or more distal repositionable structures are constrained from moving as needed in order to implement the commanded motion and also maintain the field of view. The constraint can be a range of motion (ROM) limit due to physical limitations of the repositionable structures, an obstacle, and/or the like. Additionally or alternatively, the commanded motion could cause the distal portion of the imaging device to enter a certain restricted region in the workspace. The distal portion of the imaging device can include the distal end of the imaging device, such as an imaging end of the imaging device. For example, a constraint could restrict the distal portion of the imaging device to penetrate an entry into the workspace no deeper than a specified distance. The commanded motion could cause the distal portion of the imaging device to penetrate the entry deeper than the specified distance. In such cases, the control module determines the location of the distal portion of the imaging device based on the joints and the known geometry of the repositionable structures and/or supported instruments. In some cases, such constraints are employed to restrict the imaging device from penetrating a workspace beyond a certain depth, to restrict the imaging device from getting close enough to an object in the workspace as to overheat the object, and/or the like. In other examples, motion of the repositionable structures is constrained so as to avoid collision with nearby objects, such as components, devices, and/or personnel, to avoid keep-out zones, and/or the like.

In general, the field of view is the extent of the observable world that is effectively detectable and displayable by the imaging device. The field of view of the imaging device varies based on the position and/or orientation of the imaging device, the type and size of the lens of the imaging device, the zoom setting of the lens, the focal length of the lens, and/or the like. In such circumstances where the one or more joints are not able to maintain the field of view due to a constraint, further movement of the proximal repositionable structure in a manner that would require movement of the imaging device past the constraint can no longer be compensated by the one or more joints. Such further movement of the proximal repositionable structure would result in a change in the location, i.e., the orientation and/or position, of the imaging device or field of view of the imaging device. As a result, even though the proximal repositionable structure has additional range to produce motion that moves the one or more second instruments, the proximal repositionable structure is prevented from moving due to a constraint associated with the field of view of the imaging device.

A potential approach for responding to the inability to maintain the field of view due to a constraint is to disallow motion of the proximal repositionable structure that would require movement of the one or more joints past the constraint, and thus maintaining a fixed field of view whether or not the one or more joints are subject to the constraint. As a result, the system does not allow the operator to command further movement of the one or more second instruments involving motion of the proximal repositionable structure that requires movement of the one or more joints that cause violation of the constraint. This approach can limit the achievable positions, orientations, or motions of a second instrument; can require that the operator adjust the physical configuration of the proximal or distal repositionable structures to allow the second instrument to carry out the command; or can prevent the operator from completing a desired motion or task with a second instrument.

Another potential approach for responding to the inability to maintain the field of view is to continue to compensate for the movement of the proximal repositionable structure to some defined extent. For example, some embodiments are configured to compensate as much as possible for the movement of the proximal repositionable structure. With this potential approach, the imaging device, or the field of view of the imaging device, is changed as the proximal repositionable structure moves the imaging device in a way for which the one or more joints can no longer compensate due to the constraint. This results in a floating field of view as the constraint causes the field of view to change as movement of the proximal repositionable structure that cannot be compensated for by the one or more joints continues to occur. This approach can be beneficial in some instances and can cause fewer desirable effects in other instances.

For example, in some instances, such a resulting change in the field of view relative to the workspace and/or world frame can decrease efficiency, increase the time required to perform a procedure, misalign or otherwise misdirect the field of view, be disorienting or unintuitive for a viewer of the images captured by the imaging device (e.g., the operator or another person when viewing such images), etc. Also, in some examples, such a change in the field of view causes an object upon which the operator is performing a procedure, an instrument that the operator is controlling, or an object that the operator is observing, to move out of an area of visual attention of the operator in the field of view, or out of the field of view entirely. If an object and/or an instrument moves out of the field of view (or out of a preferred location in the field of view), then the operator may have to interrupt the procedure until the object and/or instrument is again within the field of view (or at the preferred location), or to perform additional tasks to bring the object and/or instrument back into the field of view (or to the preferred location). Further, such a resulting change in the field of view can decrease efficiency in the operator having to reorient to the changed field of view, to reposition the imaging device, to reposition instruments, and the like. As a specific example, in some instances, a 90 degree clockwise rotation of the field of view can cause an operator to mistake rightward movement to be downwards, and a 180 degree rotation of the field of view can cause an operator to mistake movements to in an opposing direction. Further, such changes in the field of view can be directed in a manner that is less effective for visualizing an object to be manipulated, an instrument being commanded, the work site, or the operating environment. Such changes in the field of view, in some instance, can also confuse an operator who is accustomed to visualizing a workspace, such as anatomy, with a certain orientation.

In general, a workspace can be any region within the observable world that is accessible by the computer-assisted system. The workspace can include a worktable or bench, a chamber, a device, a portion of anatomy of a medical patient, and/or the like. Where the viewer is the operator commanding motion of the system, this change in the field of view can result in slowed operator commands to the system (and increased procedure time), decrease the perceived responsiveness of the system to operator commands, increases the tolerance and clearance needed to perform a procedure, and the like. In some instances, unexpected changes in the field of view of the imaging device can give a viewer the impression that objects viewable by the imaging device (e.g., other objects in the workspace, such as manual instruments, or patient tissue in a medical example, are moving even though they are stationary relative to the workspace, are moving differently relative to the workspace than they actually are, and the like. In some instances where motion of the imaging device results, the imaging device can collide with objects, such as patient tissue in a medical example, resulting in unintentional contact with, pressure on, and/or damage to such objects.

Some embodiments of the disclosure include techniques for enabling limited movement of an imaging device and/or field of view of the imaging device when the one or more joints of a computer-assisted system can no longer compensate for the movement of the proximal repositionable structure due to a constraint. In so doing, the computer-assisted system maintains a partially constrained field of view, allowing for limited deviation of the field of view as further described below, while also allowing the repositionable structure to continue to move, thereby allowing greater range of motion for the one or more second instruments. In some examples, maintaining a partially constrained field of view enables the operator to complete the procedure in less time or with less operator input, relative to other approaches.

When maintaining a partially constrained field of view, the computer-assisted system maintains a defined geometric relationship between a first geometric feature that is fixed relative to the imaging device and a second geometric feature that is fixed relative to the workspace. In some examples, the first geometric feature is the optical axis of the imaging device, the second geometric feature is fixed relative to a workspace (e.g., at a fixed location in the workspace, where the location may move with translation or rotation of the workspace), and the defined geometric relationship is the concurrency of the two (i.e., the optical axis must pass through the point). The computer-aided system maintains the concurrency relationship as the proximal and distal repositionable structures move. This results in changing a position, a direction of view, or both, of the imaging device. Maintaining a partially constrained field of view is less restrictive than maintaining a fixed field of view, while reducing the amount of disruption to the field of view that can result from maintaining a floating field of view. In some examples, when the second geometric feature is a point at a large distance (effectively at infinity) from the imaging device, maintaining a partially constrained field of view permits motion of the repositionable structure as long as an orientation of the imaging device (i.e., a direction of view of the imaging device) remains fixed. Additional examples of maintaining a partially constrained field of view are discussed in further detail below.

In some examples, a geometric feature could comprise a simple geometric element, such as a line segment (or a line that includes such a line segment), a point, and/or the like. A line segment can be straight or curved. Alternatively or in addition, a geometric feature could comprise a more complex element, such as a two-dimensional (2D) feature such as a parabola, a hyperbola, an ellipse, a circle, a polygon, a piecewise linear or nonlinear curve, a plane, etc. Further, alternatively or in addition, a geometric feature could comprise a three-dimensional (3D) feature such as a cone, a polygon, a sphere, a three-dimensional region of space with linear or non-linear edges or surfaces, etc. The geometric feature may also change with changes in the operating environment, operating mode of the system, stage of a procedure being performed by the system, user preference, etc.

In some examples, the defined geometric relationship could comprise a simple geometric relationship, such as concurrence. In a concurrence, at least some part of the first geometric feature coincides positionally with at least some part of the second geometric feature. For example, a point being coincident with another point, being intersected by a line, lying in a plane, or being with a region in space, are all examples of the point having concurrence with another geometric feature. Other examples of concurrence include a line segment (or lines) being colinear and overlapping another line, intersecting or lying in a plane, intersecting or lying within a region in space; a two-dimensional feature (e.g. a polygon, conic section, other two dimensional shape, a plane, etc.) intersecting or overlapping with another geometric feature. Additional examples include the intersection or overlap of other one-dimensional, two-dimensional, or three-dimensional geometric features. A defined geometric relationship could also comprise parallelism, where the first geometric feature is parallel to the second geometric feature. Specific examples of parallelism include parallel lines, lines being parallel to two-dimensional regions or planes, etc. In some instances, a defined geometric relationship is achieved when part of the first and second geometric features have such a defined geometric relationship. In some instances, a defined geometric relationship is achieved only when all of the first and second geometric features have such a defined geometric relationship. Many other defined geometric relationships exist, including orthogonality, minimum, maximum, or target separation distances, etc. Further, a defined geometric relationship could comprise multiple such relationships. More generally, the defined geometric relationship could include constraints on relative velocities between the first geometric feature and the second geometric feature.

Figure 3:
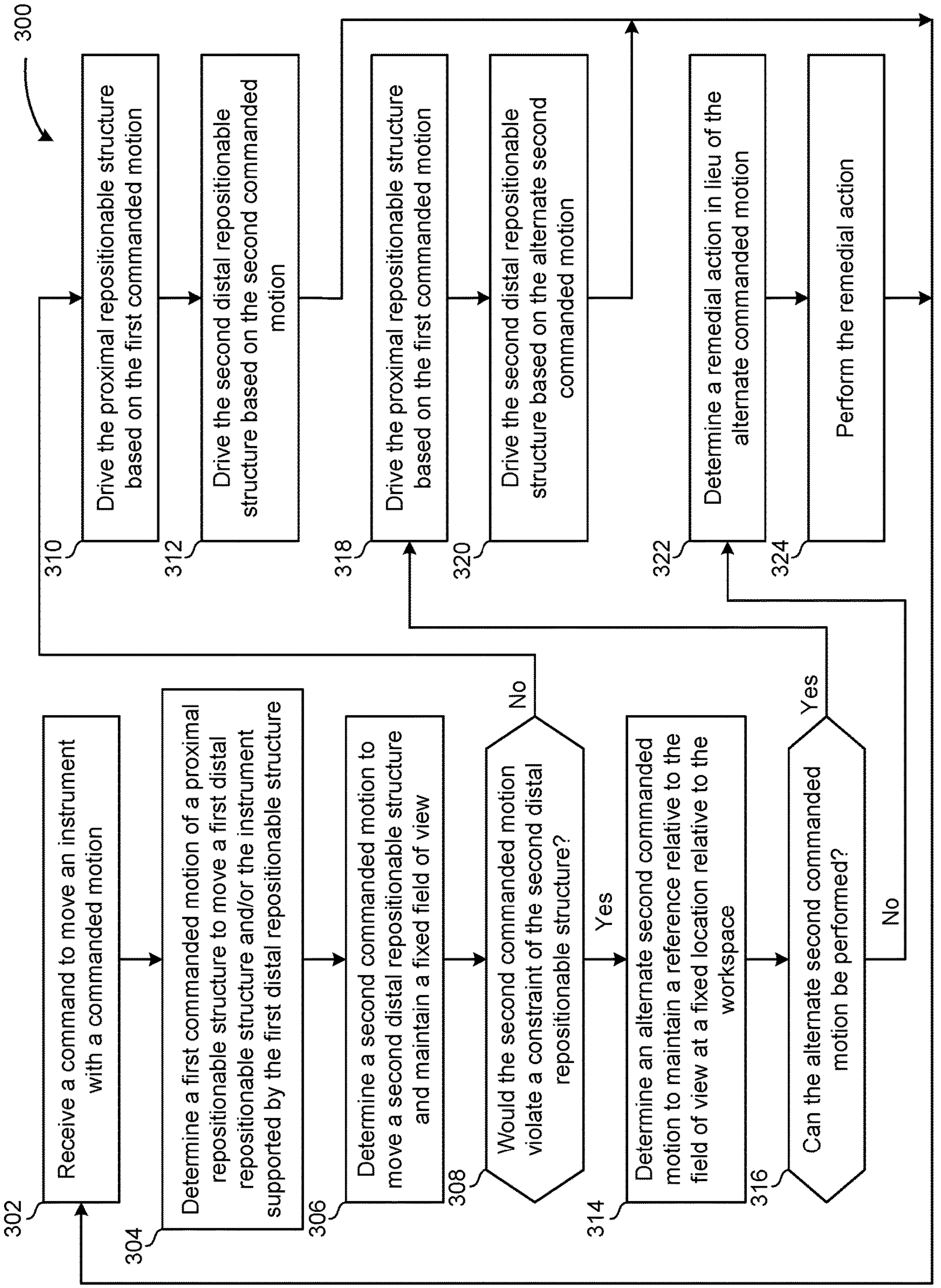
FIG. 3 is a flow diagram of method steps for controlling movement of repositionable structures that are subject to constraints in accordance with one or more embodiments.

FIG. 3 is a flow diagram of method steps for controlling movement of repositionable structures that are subject to constraints in accordance with one or more embodiments. Although the method steps are described in conjunction with the systems of FIGS. 1-2 and the examples of 4A-7D, persons of ordinary skill in the art will understand that any system configured to perform the method steps, in any order, is within the scope of the present disclosure. One or more of the processes 302-324 of method 300 can be implemented, at least in part, in the form of executable code stored on non-transient, tangible, machine-readable media. This executable code, when executed by a processor system (e.g., the processor system 150 in the control unit 140), can cause the processor system to perform one or more of the processes 302-324. In some embodiments, method 300 can be performed by a module, such as the control module 170. In some embodiments, method 300 can be applied to one or more proximal repositionable structures and/or one or more distal repositionable structures of a computer-assisted system to maintain a partially constrained field of view of an imaging device. The computer-assisted system maintains the partially constrained field of view when a fixed field of view can no longer be maintained due to a constraint associated with one or more distal repositionable structure(s) coupled to the imaging device in.

Figure 4C:
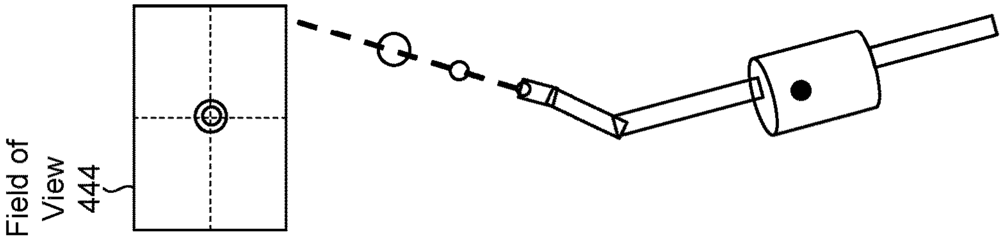
FIGS. 4A-4C illustrate movement of one or more joints of a distal repositionable structure while maintaining a fixed field of view in accordance with one or more embodiments.
Figure 4B:
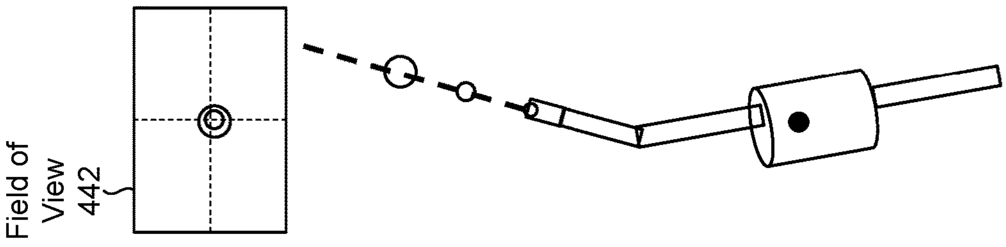
Figure 4A:
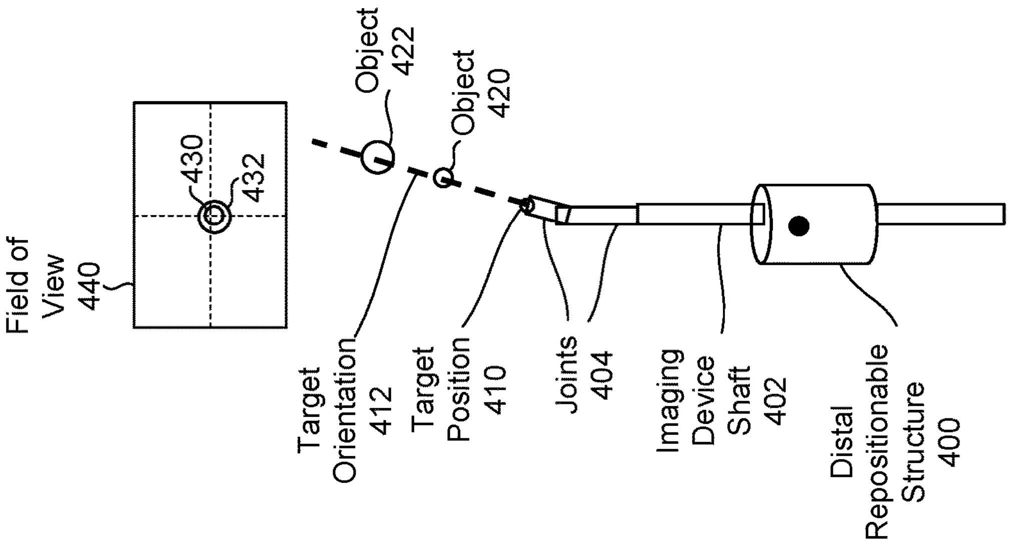

Aspects of method 300 are described via reference to FIGS. 4A-4C, which illustrate movement of one or more joints of a distal repositionable structure while maintaining a fixed field of view in accordance with one or more embodiments. Further, aspects of method 300 are described via reference to FIGS. 5A-5D, which illustrate movement of one or more joints of a distal repositionable structure while maintaining a partially constrained field of view accordance with one or more embodiments. Further, aspects of method 300 are described via reference to FIGS. 6A-6D, which illustrate movement of one or more joints of a distal repositionable structure while maintaining a partially constrained field of view at infinity in accordance with one or more embodiments. Further, aspects of method 300 are described via reference to FIGS. 7A-7D, which illustrate movement of one or more joints of a distal repositionable structure while maintaining a floating field of view in accordance with one or more embodiments. However, it is understood that the examples of FIGS. 4A-4C, FIGS. 5A-5D, FIGS. 6A-6D, and FIGS. 7A-7D are not restrictive, and that other values, shapes, behaviors, and/or the like depicted in FIGS. 4A-4C, FIGS. 5A-5D, FIGS. 6A-6D, and FIGS. 7A-7D may be different for different input controls 252, different repositionable structures, different follower instruments, different DOFs, different procedures, different viewable objects, and/or the like.

At a process 302, a control module, such as control module 170, receives a command to move a proximal repositionable structure with a commanded motion. In some examples, the commanded motion of the proximal repositionable structure is determined to move an instrument supported by a distal repositionable structure. The control module 170 can receive the command via any technically feasible techniques, such as by detecting an input from one or more input controls 252, in response to being manipulated by the operator 298, receiving an input from a semi-autonomous or autonomous software application executed by the processor system (e.g., the processor system 150 in the control unit 140), and/or the like. The control module 170 can operate in teleoperated mode, in semi-autonomous, or autonomous mode. The control module 170 can operate in a single mode during a procedure or may switch among multiple modes during a procedure.

In teleoperated mode, the control module 170 receives the command from the operator 298 via one or more input controls, such as the one or more input controls 252. For example, the input controls 252 are contacted and manipulated by the hands of the operator 298, such as with one input control 252 for each hand. In semi-autonomous mode, the control module 170 receives commands from a software application executed by the processor system as well as from the operator 298 via the one or more input controls 252. In some examples, the control module 170 receives commands from the operator 298 during certain steps of the procedure and received commands from the software application during certain other steps of the procedure. Additionally or alternatively, the control module 170 receives commands from the software application, where the operator 298 can override the software application and generate commands via one or more input controls 252. During autonomous operation, the control module 170 generally receives commands from the software application during the entire procedure.

At a process 304, the control module determines a first commanded motion of a proximal repositionable structure to move a first distal repositionable structure and/or the instrument supported by the first distal repositionable structure. The proximal repositionable structure is located proximal to multiple distal repositionable structures such that movement of the proximal repositionable structure causes movement of the multiple distal repositionable structures including the first distal repositionable structure.

More specifically, the first distal repositionable structure can be subject to certain constraints, such that the first distal repositionable structure cannot be moved according to the commanded motion. In such cases, the proximal repositionable structure is moved instead of or in addition to the first distal repositionable structure, such that the combined movement of the proximal repositionable structure and the first distal repositionable structure moves the instrument according to the commanded motion, as described in conjunction with FIG. 2.

When determining the first commanded motion of the proximal repositionable structure(s), the control module performs calculations using kinematic models and/or the Jacobian for each of the proximal repositionable structures, distal repositionable structures, and/or the instruments. The control module uses these calculations to generate various numerical parameters of the joints, including joint position, velocity, and/or acceleration, as detected by joint sensors. These numerical parameters are then used to drive one or more joints of the proximal repositionable structures, the distal repositionable structures, and/or the instruments based on the first commanded motion.

In some examples, a second distal repositionable structure of the multiple distal repositionable structures is configured to support an imaging device. The imaging device can include one-dimensional (1D), 2D, 3D, or higher dimensional imaging capabilities. Examples of medical imaging devices include endoscopes and ultrasound probes. Additional examples of imaging devices include optical cameras, cameras that image in the visible light spectrum, infrared spectrum, ultraviolet spectrum, RF spectrum (e.g. a gamma probe), a hyperspectral spectrum, and/or the like. In operation, movement of the proximal repositionable structure can be used to produce motion that moves, or assists in the movement of, the one or more second instruments supported by the second distal repositionable structure.

At a process 306, the control module determines a second commanded motion to move a second distal repositionable structure to maintain a fixed field of view for an imaging device. The motion of the proximal repositionable structure described in process 304 can also move the second distal repositionable structure supporting an imaging device, and thus motion of the proximal repositionable structure can also move the imaging device. As a result, the field of view of the imaging device also moves, which can be disorienting or unintuitive to the operator 298. Therefore, the second distal repositionable structure coupled to the imaging device moves in a manner so as to maintain the field of view of the imaging device. To maintain an orientation, a position, or both an orientation and a position, of the imaging device or the field of view of the imaging device, the control module commands movement of one or more joints of the imaging device and/or the supporting second distal repositionable structure while commanding movement of the proximal repositionable structure. When determining the second commanded motion of the second distal repositionable structure, the control module performs calculations using kinematic models and/or the Jacobian for each of the distal repositionable structures, distal repositionable structures, and/or the instruments. The control module uses these calculations to generate various numerical parameters of the joints, including joint position, velocity, and/or acceleration, as detected by joint sensors. These numerical parameters are used to drive one or more joints of the proximal repositionable structures, the distal repositionable structures, and/or the instruments based on the second commanded motion.

FIGS. 4A-4C illustrate movement of one or more joints of a distal repositionable structure 400 while maintaining a fixed field of view in accordance with one or more embodiments. In some examples, the distal repositionable structure 400 corresponds to the second distal repositionable structure of process 306. As shown in FIG. 4A, an imaging device shaft 402 is coupled to joints 404 of the distal repositionable structure 400. The imaging device shaft 402 is coupled to the joints 404 which are set to a position and orientation such that the distal portion of the imaging device is at a target position 410 and with a target orientation 412. As shown, the target orientation 412 passes through the center of a first object 420. Correspondingly, the image 430 of the first object 420 is at the center of the field of view 440. Similarly, the target orientation 412 passes through the center of a second object 422. Correspondingly, the image 432 of the second object 422 is also at the center of the field of view 440. As shown in FIG. 4B, the imaging device shaft 402 has moved as a result of a movement of a proximal repositionable structure (not shown). In some examples, the movement of the proximal repositionable structure has moved, or assisted in the movement of, the first distal repositionable structure that supports an instrument. In response, the joints 404 have moved in order to maintain the target position 410 and the target orientation 412 of the imaging device. Correspondingly, the image 430 of the first object 420 and the image 432 of the second object 422 remain fixed relative to the field of view 442. As shown in FIG. 4C, the imaging device shaft 402 has further moved as a result of an additional movement of the proximal repositionable structure. In response, the joints 404 have further moved in order to maintain the target position 410 and the target orientation 412 of the imaging device. Correspondingly, the image 430 of the first object 420 and the image 432 of the second object 422 remain fixed relative to the field of view 444. The motion of the joints 404 to maintain the fixed field of view corresponds to the second commanded motion to move the second distal repositionable structure and/or the imaging device determined during process 306.

At a process 308, the control module determines whether the second commanded motion would cause the distal repositionable structure 400 to violate a constraint. In some examples, the second distal repositionable structure is constrained from moving as needed in order to implement the commanded motion. In particular, one or more joints of the distal repositionable structure 400 can be constrained and/or limited by a range of motion (ROM) limit due to physical limitations. Additionally or alternatively, the second commanded motion could cause the distal portion of the imaging device to enter a certain restricted region in the workspace. For example, a constraint could restrict the distal portion of the imaging device to penetrate an entry into the workspace no deeper than a specified distance. The second commanded motion could cause the distal portion of the imaging device to penetrate the entry deeper than the specified distance. In such cases, the control module can determine the location of the distal portion of the imaging device based on the joints and the known geometry of the repositionable structures and/or supported instruments. In other examples, motion of the distal repositionable structure 400 can be constrained so as to avoid collision with nearby objects, such as components, devices, and/or personnel, to avoid keep-out zones, and/or the like.

If the control module determines that the second commanded motion would violate a constraint of the distal repositionable structure 400, then the method proceeds to a process 314. If the control module determines that the second commanded motion would not violate a constraint of the distal repositionable structure 400, then the method 300 proceeds to a process 310, where the control module drives the proximal repositionable structure based on the first commanded motion. During process 310, driving the proximal repositionable structure includes driving the joints of the proximal repositionable structure, using the corresponding numerical parameters determined during process 304. In some examples, the numerical parameters are provided as setpoints to one or more control systems or controls used to control the joints of the proximal repositionable structure.

At a process 312, the control module drives the distal repositionable structure 400 based on the second commanded motion. During process 312, driving the second distal repositionable structure can involve driving the individual joints of the second distal repositionable structure, using the corresponding numerical parameters determined during process 306. In some examples, the numerical parameters are provided as setpoints to one or more control systems or controls used to control the joints of the second distal repositionable structure. The method 300 then returns to process 302, described above to handle other commanded motions of the instrument.

Returning to process 308, if the control module determines that the second commanded motion would cause the distal repositionable structure 400 to violate a constraint, then the method 300 proceeds to a process 314, where the control module determines an alternate second commanded motion to maintain a defined geometric relationship between a first geometric feature fixed relative to the imaging device and in the field of view, and a second geometric feature fixed relative to the workspace. The geometric features and the defined geometric relationship between the geometric features are determined such that at least one degree of freedom of the imaging device is restricted (e.g., of a distal portion of the imaging device or a field of view of the imaging device). In some examples, the geometric features and the defined geometric relationship between the geometric features are determined such that fewer than all six degrees of freedom of the imaging device distal portion or field of view are restricted. For example, in some instances, one, two, or three translational degrees of freedom are not restricted, and/or one, two, or three rotational degrees of freedom are not restricted (but at least one degree of freedom is restricted). Thus, the geometric features and the defined geometric relationship between the geometric features are determined such that the imaging device is not allowed to move completely free of any restrictions.

In some embodiments, the first geometric feature is the optical axis of the imaging device, and the second geometric feature is a fixed location in the workspace). The control module applies the defined geometric relationship to maintain the concurrency of the geometric features. In this example, the defined geometric relationship of concurrency means that the optical axis (the first geometric feature) passes through the fixed location in the workspace (the second geometric feature). As a result, an object positioned and kept at the fixed location would appear, in the images captured by the imaging device, to be static as the field of view of the imaging device moves, while the system maintains a partially constrained field of view. Further, an object positioned and kept at a location closer to the distal portion of the imaging device than the fixed location would appear, in the images captured by the imaging device, to drift in the opposite direction relative to the direction of movement of the field of view of the imaging device. An object positioned and kept at a location farther from the distal portion of the imaging device than the fixed location would, in the images captured by the imaging device, appear to drift in the same direction relative to the direction of movement of the field of view of the imaging device.

In an example process, the control module determines a first geometric feature fixed relative to the imaging device (e.g. fixed in position relative to a part of the imaging device, to a field of view of the imaging device, etc., even as such part or field of view moves). Examples of such a first geometric feature include those described above, and also: the optical axis of the imaging device, a point on the optical axis of the imaging device, a line formed by joining the distal portion of the imaging device to the distal portion of an instrument (determined at the time of commencing the partially constrained field of view state), and/or the like. Additionally or alternatively, the first geometric feature can include a coordinate frame that is fixed with respect to a distal portion of the imaging device. For example, a coordinate frame, such as a triad of x, y, and z axes can function as the first geometric feature fixed relative to the imaging device. In some examples, the origin of the coordinate frame is at the distal tip of the imaging device and the z-axis of the coordinate frame coincides with the optical axis. The coordinate frame is fixed with respect to the distal portion of the imaging device and maintains a constant orientation relative to the workspace.

In the example process, the control module registers a second geometric feature fixed relative to the workspace via one or more techniques described herein. Examples of such a second geometric feature include those described above, and also: a fixed location in the workspace, a fixed line in the workspace, the entire workspace, and/or the like. In some examples, the control module is configured to determine the second geometric feature based on a location of a distal portion of an instrument. The control module determines the location as of the time of commencing the partially constrained field of view technique, and/or prior to driving the repositionable structure or the one or more joints when using the partially constrained field of view technique. In some instances, the partially constrained field of view technique is associated with a mode of the control module. In some instances, the partially constrained field of view technique is not associated with a particular mode and is used when the system cannot move the field of view entirely as commanded.

In some examples, the control module is configured to determine the second geometric feature based on the location(s) of one or more distal portions of a plurality of instruments supported by the repositionable structure. The control module determines the locations as of the time of commencing the partially constrained field of view technique and/or prior to driving the repositionable structure or the one or more joints when using the partially constrained field of view technique. In some examples, the control module determines the second geometric feature to be a fixed location in the workspace and defines this point based on a line that extends from the distal portion of the imaging device in a direction based on the orientation of the imaging device at a defined instant in time. The control module establishes the second geometric feature at a point along this line at a specified distance from the distal portion of the imaging device. In some examples, the specified distance is fixed at the midpoint of the focal distance of the imaging device. In some instances, the midpoint represents a region in the workspace where a procedure is likely being performed by the operator. In some examples, the specified distance is based on a depth sensor located on the imaging device that determines the depth of the anatomy or other object in the workspace. In some examples, the specified distance is based on the average location of a set of instruments supported by the repositionable structure(s). In such examples, the specified distance is dynamic and changes as the position and/or orientation of the instruments change. In some examples, the specified distance is set based on the type of procedure being performed by the operation. In some examples, the fixed location in the workspace is located at a reference distance from the distal portion of the imaging device and lies on an optical axis of the imaging device when the control module initiates a state of maintaining a partially constrained field of view.

In some embodiments, the control module determines the second geometric feature fixed relative to the workspace to be a point based on the location of the distal portions of one or more instruments, including any one or more of multiple instruments being supported by the distal repositionable structures. In a specific example, the second geometric feature comprises a point fixed relative to the workspace. In some examples, the control module determines the fixed location based on the first instrument introduced to the workspace and/or any one or more subsequent instruments introduced to the workspace. In some examples, the control module determines the fixed location based on multiple instruments. In some examples, the control module determines the vertices of a polygon where each vertex of the polygon represents the location of the distal portion of a different instrument. In some examples, the control module establishes the fixed location based on a representative location that corresponds to an average location of the vertices of the polygon, the centroid of the polygon, the center of the smallest disk that includes all of the vertices of the polygon, and/or the like. In some examples, the control module restricts the selection of instruments on which to base the fixed location based on the type of the instrument and/or the geometry of the instrument. In some examples, the control module bases the fixed location on a static location of the distal portion of the instrument. In such examples, the control module receives the static location of the instrument as positioned by the operator 298 in order to designate the fixed location. In some examples, the control module bases the fixed location on a dynamic motion of the distal portion of the instrument, such as a trace of the distal portion location of the instrument around a desired fixed location.

In some examples, the control module sets a fixed location based on the insertion depths of one or more instruments. In some examples, the control module establishes the fixed location based on the arithmetic mean of the depths of the multiple instruments, the geometric mean of the depths of the multiple instruments, the median depth of the multiple instruments, the instrument with the longest depth, the instrument with the shortest depth, and/or the like.

In some examples, the control module bases the fixed location on a focal distance of the imaging device. In some instances, the focal distance is the depth of focus of the imaging device, and the fixed location can be a point at this depth along the optical axis of the imaging device. In some examples, the focal distance for certain imaging devices is fixed, in which case the fixed location is at a fixed distance relative to the distal portion of the imaging device. In other examples, the depth of focus for certain imaging devices is operator adjustable. In such cases, the control module bases the fixed location on the current setting of the depth of focus of the imaging device.

In some embodiments, the control module bases the fixed location on the location of at least one viewable feature in the field of view of the imaging device. The viewable feature can include an object in the workspace, a fixture associated with one or more instruments, and/or the like. In some examples, the viewable feature can include a fiducial indicator that appears as a marker on an object or fixture in the field of view of the imaging device. In some medical examples, the control module bases the fixed location on the position of an object that includes a portion of anatomy. In some examples, the control module bases the fixed location on the position of a fixture that includes a device for retracting, holding, and/or moving an object, such as a portion of anatomy of a medical patient.

In some examples, the position, including depth, of an object, fixture, or other fiducial indicia is determined via a 3D/stereoscopic imaging device. In some examples, the position, including depth, of an object, fixture, or other fiducial indicia is determined via analysis of multiple images captured by the imaging device as the imaging device is moved. In some examples, the second geometric feature is based on the type of imaging device. In some examples, the second geometric feature is based on the particular procedure being performed.

In some embodiments, the operator 298 specifies the first geometric feature that is fixed relative to the imaging device and the second geometric feature that is fixed relative to the workspace via a user interface. Additionally or alternatively, the operator 298 activates an input to register the first geometric feature that is fixed relative to the imaging device and the second geometric feature that is fixed relative to the workspace, such as by pressing a button, issuing a voice command, activating a control on a user interface, and/or the like. Subsequent to specifying the first geometric feature that is fixed relative to the imaging device and the second geometric feature that is fixed relative to the workspace, the control module generates a mapping, where the mapping is a defined geometric relationship between the first geometric feature and the second geometric feature. The control module can generate the defined geometric relationship at any time prior to performing the processes of method 300 and/or during the performance of the processes of method 300.

In some embodiments, the control module determines the fixed location based on a line that is fixed relative to the imaging device at a point that intersects a fixed line in the workspace at a defined instant of time, such as when commencing a partially constrained field of view. The control module can determine this fixed line in the workspace by determining a line between two fixed locations in the workspace, determining a line between the geometric features within the workspace, and/or the like.

In general, the control module determines a defined geometric relationship between the first geometric feature that is fixed relative to the imaging device and the second geometric feature that is fixed relative to the workspace. This defined geometric relationship is maintained throughout the process of maintaining the partially anchored field of view. As discussed herein, the relationship could be concurrency, parallelism, the constancy of relative orientation, the constancy of angular velocity in a defined direction, and/or the like. In some examples, the defined geometric relationship could be a composite relationship. For example, if the first geometric feature is a coordinate frame attached to the distal tip of the imaging device, and the second feature is a fixed location in the workspace, the control module could maintain that a) the angular velocity of the first geometric feature (the coordinate frame) about its z axis is zero, and b) the z axis of the first geometric feature (the coordinate frame) is concurrent with the second geometric feature (i.e., the fixed location in the workspace).

Figures 5A, 5B:
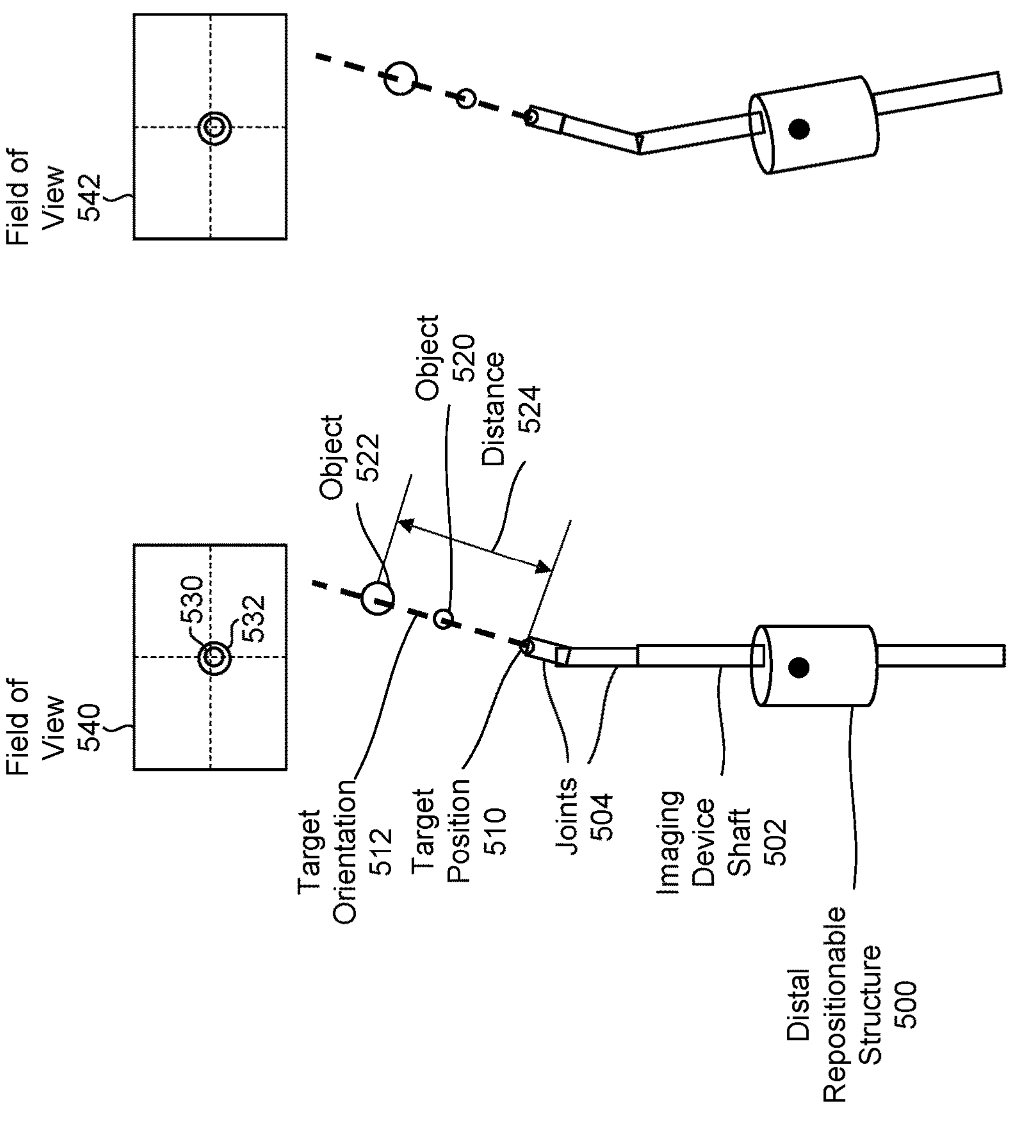
FIGS. 5A-5D illustrate movement of one or more joints of a distal repositionable structure while maintaining a partially constrained field of view accordance with one or more embodiments.

FIGS. 5A-5D illustrate movement of one or more joints of a distal repositionable structure while maintaining a partially constrained field of view in accordance with one or more embodiments. In some examples, the distal repositionable structure 500 corresponds to the second distal repositionable structure of process 314 As shown in FIG. 5A, an imaging device shaft 502 is coupled to joints 504 of the distal repositionable structure 500. The imaging device shaft 502 is coupled to the joints 504 which are set to a position and orientation such that the distal portion of the imaging device is at a target position 510 and with a target orientation 512. As shown, the target orientation 512 passes through the center of a first object 520. Correspondingly, the image 530 of the first object 520 is at the center of the field of view 540. Similarly, the target orientation 512 passes through the center of a second object 522. Correspondingly, the image 532 of the second object 522 is also at the center of the field of view 540. The second object 522 is positioned at a reference distance 524 from the distal portion of the imaging device. As shown in FIG. 5B, the imaging device shaft 502 has moved as a result of a movement of a proximal repositionable structure (not shown). In some examples, the movement of the proximal repositionable structure has moved, or assisted in the movement of, the first distal repositionable structure that supports an instrument. In response, the joints 504 have moved in order to maintain the target position 510 and the target orientation 512 of the imaging device. Correspondingly, the image 530 of the first object 520 and the image 532 of the second object 522 remain fixed relative to the field of view 542.

Figure 5C:
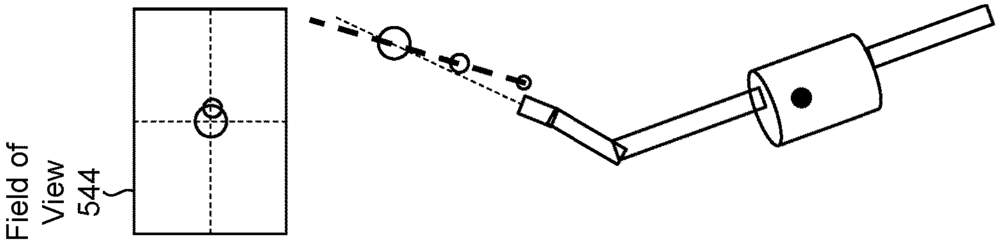

As shown in FIG. 5C, the imaging device shaft 502 has further moved as a result of an additional movement of the proximal repositionable structure. In response, the joints 504 have further moved, but are not able to maintain the target position 510 and the target orientation 512 of the imaging device. Instead, a partially constrained field of view 544 is maintained such that the image 532 of the second object remains fixed relative to the partially constrained field of view 544. As discussed in conjunction with process 314, the control module maintains a defined geometric relationship between the first geometric feature that is fixed relative to the imaging device and the second geometric feature that is fixed relative to the workspace. As shown, the second geometric feature is a point in the field of view 544 at a fixed reference distance 524 from the first geometric feature, such as the distal portion of the imaging device and lying on the optical axis, shown as the target orientation 512, of the imaging device. Objects closer to the first geometric feature than the reference distance to the second geometric feature appear to drift in the opposite direction relative to the direction of movement of the imaging device. Objects farther from the first geometric feature than the reference distance to the second geometric feature appear to drift in the same direction relative to the direction of movement of the imaging device. In particular, the first object 520 is located closer to the distal portion of the imaging device relative to the reference distance 524. Correspondingly, as the joints 504 have further moved to the left, the image 530 of the first object 520 appears to move to the right relative to the partially constrained field of view 544.

Figure 5D:
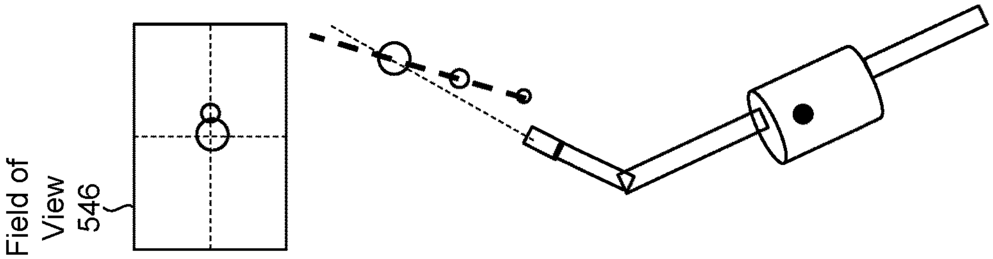

As shown in FIG. 5D, the imaging device shaft 502 has further moved as a result of an additional movement of the proximal repositionable structure. In response, the joints 504 have further moved, but are still not able to maintain the target position 510 and the target orientation 512 of the imaging device. Instead, a partially constrained field of view 546 is maintained such that the image 532 of the second object remains fixed relative to the partially constrained field of view 546. The first object 520 is located closer to the distal portion of the imaging device relative to the reference distance 524. Correspondingly, the image 530 of the first object 520 appears to move farther to the right relative to the partially constrained field of view 546. The motion of the joints 504 to maintain the partially constrained field of view corresponds to the alternate second commanded motion to move the second distal repositionable structure and/or the imaging device determined during process 314.

Referring back to process 314, in some embodiments with a first geometric feature comprising the optical axis, the second geometric feature comprising a fixed location in the work space, and a defined geometric relationship comprising concurrency, the control module does the following. The control module determines an alternate second commanded motion to maintain the concurrency of the optical axis of the imaging device with the fixed location in the workspace, where the point is at a distance of infinity or at a distance that is large enough to be effectively at infinity for the operating parameters of the imaging device or for typical human visual acuity. To specify a maintenance of a partially constrained field of view at infinity, the control module sets a reference direction of view based on an input from the operator 298. In some examples, the reference direction of view is selected at any time prior to performing the processes of method 300 and/or during the performance of the processes of method 300.

In some examples, the reference direction of view is selected via one or more techniques. In some examples, the control module sets the reference direction of view as the current direction of view of the imaging device at that time that the control module begins maintaining a partially constrained field of view at infinity. In some examples, the operator selects an object in the field of view that is greater than a threshold distance from the distal portion of the imaging device. In response to the selection, the control module determines that the object in the field of view is greater than the threshold distance from the distal portion of the imaging device and begins maintaining a partially constrained field of view at infinity. The control module sets the reference direction of view based on the angle between the distal portion of the imaging device and the selected object. In some examples, the operator manually selects maintaining a partially constrained field of view at infinity mode via a user interface. In some examples, the operator manually sets the reference direction of view via a touchscreen, a stylus, a joystick, a trackball, a button cluster, and/or other input control.

Regardless of the technique employed to establish the reference direction of view, the operator specifies a reference direction of view via a user interface and/or activates an input to register the reference direction of view, such as by pressing a button, issuing a voice command, activating a control on a user interface, and/or the like. The selected reference for maintaining a partially constrained field of view at infinity is located at a reference distance of infinity or at a large distance greater than a threshold amount that is effectively infinity. Objects at a large distance from the distal portion of the imaging device are effectively located at infinity while maintaining a partially constrained field of view at infinity. Objects not at infinity are in the foreground. All objects not at infinity appear to drift in the opposite direction relative to the direction of movement of the imaging device. Objects located at infinity (or objects at a large distance greater than a threshold amount that is effectively at infinity relative to the distal portion of the imaging device) remain fixed within the field of view of the imaging device.

Figure 6A:
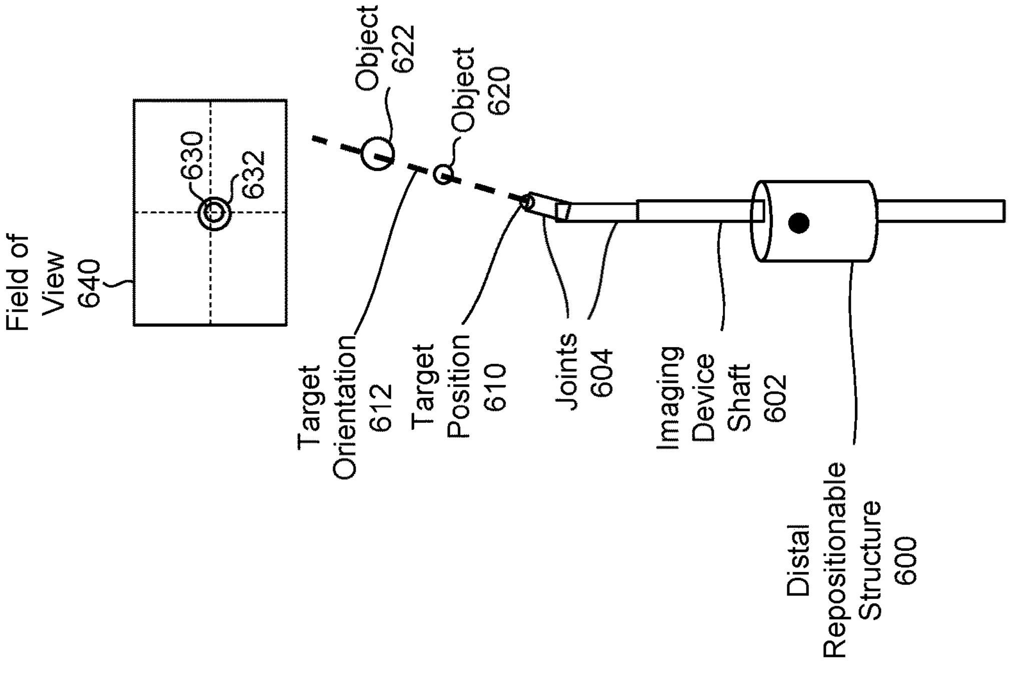
FIGS. 6A-6D illustrate movement of one or more joints of a distal repositionable structure while maintaining a partially constrained field of view at infinity in accordance with one or more embodiments.
Figure 6B:
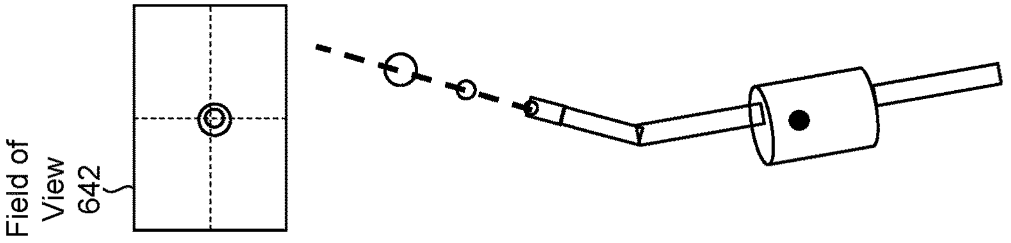

FIGS. 6A-6D illustrate movement of one or more joints of a distal repositionable structure while maintaining a partially constrained field of view at infinity in accordance with one or more embodiments. In some examples, the distal repositionable structure 600 corresponds to the second distal repositionable structure of process 314 As shown in FIG. 6A, an imaging device shaft 602 is coupled to joints 604 of the distal repositionable structure 600. The imaging device shaft 602 is coupled to the joints 604 which are set to a position and orientation such that the distal portion of the imaging device is at a target position 610 and with a target orientation 612. As shown, the target orientation 612 passes through the center of a first object 620. Correspondingly, the image 630 of the first object 620 is at the center of the field of view 640. Similarly, the target orientation 612 passes through the center of a second object 622. Correspondingly, the image 632 of the second object 622 is also at the center of the field of view 640. The target orientation 612 is set at a reference direction of view relative to the distal portion of the imaging device. As shown in FIG. 6B, the imaging device shaft 602 has moved as a result of a movement of a proximal repositionable structure (not shown). In some examples, the movement of the proximal repositionable structure has moved, or assisted in the movement of, the first distal repositionable structure that supports an instrument. In response, the joints 604 have moved in order to maintain the target position 610 and the target orientation 612 of the imaging device. Correspondingly, the image 630 of the first object 620 and the image 632 of the second object 622 remain fixed relative to the field of view 642.

Figure 6C:
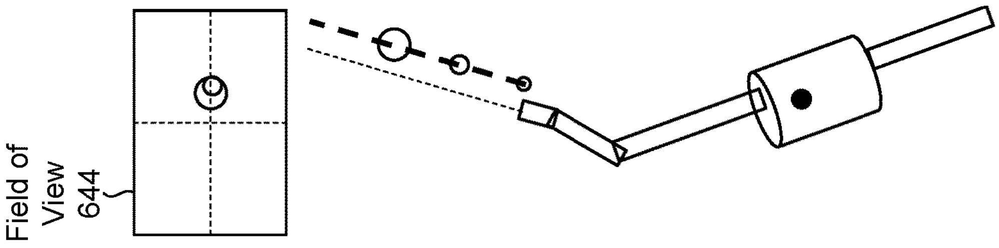

As shown in FIG. 6C, the imaging device shaft 602 has further moved as a result of an additional movement of the proximal repositionable structure. In response, the joints 604 have further moved, but are not able to maintain both the target position 610 and the target orientation 612 of the imaging device. Instead, a partially constrained field of view at infinity 644 is maintained such that the distal portion of the imaging device moves from the target position 610. However, the orientation of the imaging device is maintained at the target orientation 612, which is the reference direction of view. Both the first object 620 and the second object 622 are located less than an infinite distance from the distal portion of the imaging device. Correspondingly, the image 630 of the first object 620 and the image 632 of the second object 622 appear to move to the right relative to the partially constrained field of view at infinity 644. Because the first object 620 is closer to the distal portion of the imaging device relative to the second object 622, the image 630 of the first object 620 appears to move farther to the right relative to the image 632 of the second object 622.

Figure 6D:
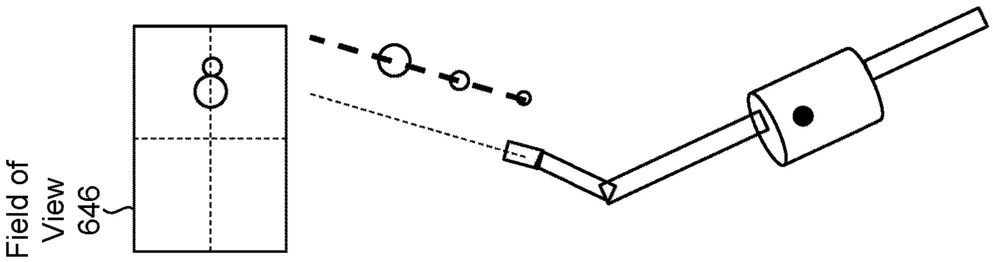

As shown in FIG. 6D, the imaging device shaft 602 has further moved as a result of an additional movement of the proximal repositionable structure. In response, the joints 604 have further moved, but are still not able to maintain the target position 610 and the target orientation 612 of the imaging device. Instead, a partially constrained field of view at infinity 646 is maintained such that the distal portion of the imaging device further moves from the target position 610. However, the orientation of the imaging device is maintained at the target orientation 612, which is the reference direction of view. Both the first object 620 and the second object 622 are located less than an infinite distance from the distal portion of the imaging device. Correspondingly, the image 630 of the first object 620 and the image 632 of the second object 622 appear to move farther to the right relative to the partially constrained field of view at infinity 646. Because the first object 620 is closer to the distal portion of the imaging device relative to the second object 622, the image 630 of the first object 620 appears to move farther to the right relative to the image 632 of the second object 622. In addition, the divergence between the image 630 of the first object 620 and the image 632 of the second object 622 is greater in the partially constrained field of view at infinity 646 of FIG. 6D relative to the partially constrained field of view at infinity 644 of FIG. 6C. The motion of the joints 604 to maintain the partially constrained field of view at infinity corresponds to the alternate second commanded motion to move the second distal repositionable structure and/or the imaging device determined during process 314.

While maintaining a partially constrained field of view, including a partially constrained field of view at infinity, the control module can disable movement of the second distal repositionable structure in certain directions and/or degrees of freedom while enabling movement of the second distal repositionable structure in other directions and/or degrees of freedom. In some examples, as further movement of the proximal repositionable structure occurs, the imaging device can continue to move as long as the reference location can be maintained within a small tolerance of the fixed location in the workspace. In various examples, the small tolerance can include a positional accuracy tolerance and an orientational accuracy tolerance. In some examples, the positional accuracy tolerance can be in the range of 0.25, 0.5, 1, or 2 cm and the orientational accuracy tolerance can be in the range of 5, 10, 20, or 30 degrees. For example, with partially constrained field of view at infinity, the control module allows the orientation to drift by up to the orientational accuracy tolerance, even though the control module is nominally holding the orientation as fixed. In some examples, a characteristic dimension of a cross section of an instrument is approximately 3 to 10 mm. Further, the instrument workspace of such an instrument can be a cylinder with a diameter of 5 cm to 20 cm or some other 3D region with a characteristic dimension larger than the characteristic dimension of the instrument. In an example where the instrument has a characteristic dimension of 5 mm, the instrument workspace is a cylinder with a diameter of 6 cm, and the positional accuracy tolerance is 1 cm, then the positional accuracy is approximately twice the instrument characteristic dimension, and approximately 17% of the diameter of the instrument workspace.

At a process 316, the control module determines whether the alternate second commanded motion can be performed while maintaining the partially constrained field of view. When maintaining a partially constrained field of view, the control module determines whether both the alternate second commanded motion can be performed and the partially constrained field of view can be maintained. In some examples, the control module determines that the partially constrained field of view can no longer be maintained due to a constraint on one or more joints, a physical limitation of the second distal repositionable structure, and/or the like. In such cases, the control module determines that the alternate second commanded motion cannot be performed.

If the control module determines that the alternate second commanded motion can be performed while maintaining the partially constrained field of view, then the method 300 proceeds to a process 318, where the control module drives the proximal repositionable structure based on the first commanded motion. During process 318, driving the proximal repositionable structure can involve driving the individual joints of the proximal repositionable structure, using corresponding numerical parameters determined during process 304. In some examples, the numerical parameters are provided as setpoints to one or more control systems or controls used to control the joints of the proximal repositionable structure.

At a process 320, the control module drives the second distal repositionable structure based on the alternate second commanded motion. During process 320, driving the second distal repositionable structure can involve driving the individual joints of the second distal repositionable structure, using corresponding numerical parameters determined during process 314. In some examples, the numerical parameters are provided as setpoints to one or more control systems or controls used to control the joints of the second distal repositionable structure. The method 300 then returns to process 302, described above to handle other commanded motions of the instrument.

Returning to process 316, if the control module determines that the alternate second commanded motion cannot be performed while maintaining the partially constrained field of view, then the method 300 proceeds to a process 322, where the control module exits maintaining the partially constrained field of view and determines a remedial action in lieu of the alternative commanded motion.

In some examples, the remedial action includes commencing a mode for maintaining a fixed field of view, as described in conjunction with processes 304-306. In so doing, the control module disallows movement of the proximal repositionable structure that would cause the one or more joints to violate the constraint. The control module continues to disallow movement of the proximal repositionable structure until a command is received that moves in a direction that would no longer result in a constraint.

In some examples, the remedial action includes commencing a mode for maintaining a floating field of view. In so doing, the control module allows movement of the proximal repositionable structure without restriction while attempting to maintain the defined geometric relationship between the first geometric feature and the second geometric feature as closely as possible given system constraints or other operational constraints. The control module continues to maintain a floating field of view until a command is received that moves in a direction that would no longer result in a constraint.

Figure 7A:
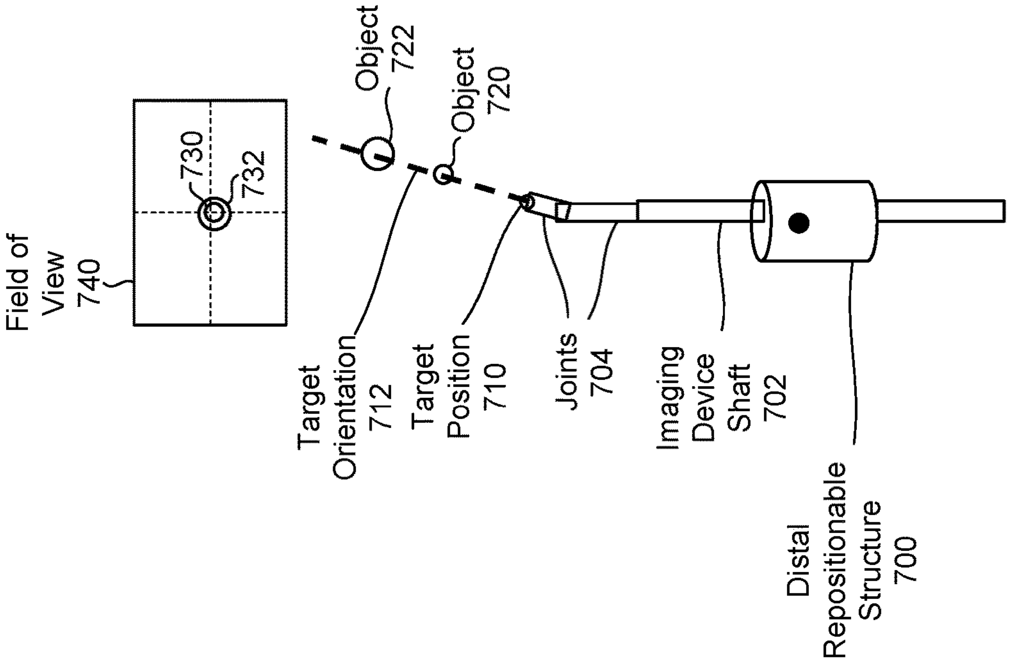
FIGS. 7A-7D illustrate movement of one or more joints of a distal repositionable structure while maintaining a floating field of view in accordance with one or more embodiments.
Figure 7B:
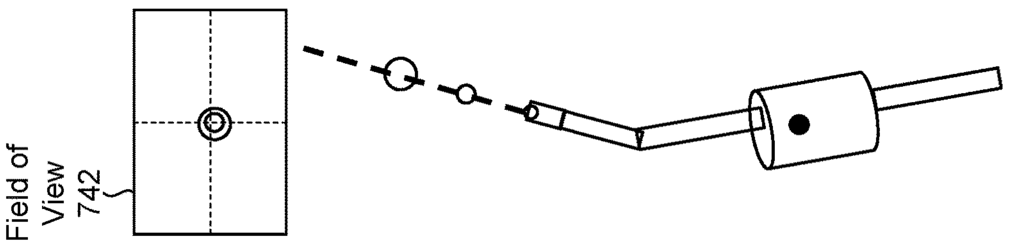

FIGS. 7A-7D illustrate movement of one or more joints of a distal repositionable structure while maintaining a floating field of view accordance with one or more embodiments. In some examples, the distal repositionable structure 700 corresponds to the second distal repositionable structure of processes 306 and 308 As shown in FIG. 7A, an imaging device shaft 702 is coupled to joints 704 of the distal repositionable structure 700. The imaging device shaft 702 is coupled to the joints 704 which are set to a position and orientation such that the distal portion of the imaging device is at a target position 710 and with a target orientation 712. As shown, the target orientation 712 passes through the center of a first object 720. Correspondingly, the image 730 of the first object 720 is at the center of the field of view 740. Similarly, the target orientation 712 passes through the center of a second object 722. Correspondingly, the image 732 of the second object 722 is also at the center of the field of view 740. As shown in FIG. 7B, the imaging device shaft 702 has moved as a result of a movement of a proximal repositionable structure (not shown). In some examples, the movement of the proximal repositionable structure has moved, or assisted in the movement of, the first distal repositionable structure that supports an instrument. In response, the joints 704 have moved in order to maintain the target position 710 and the target orientation 712 of the imaging device. Correspondingly, the image 730 of the first object 720 and the image 732 of the second object 722 remain fixed relative to the field of view 742.

Figure 7D:
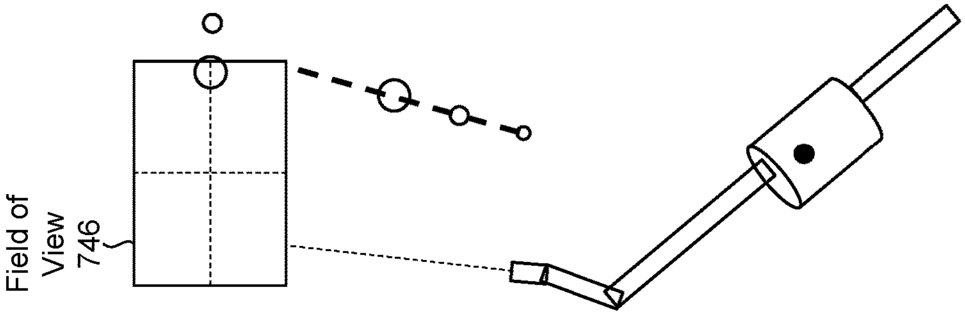
Figure 7C:
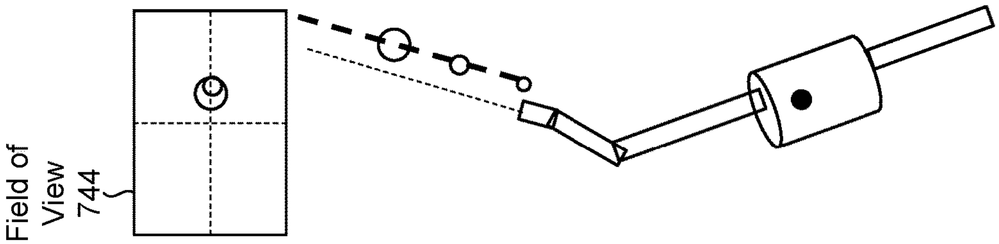

As shown in FIG. 7C, the imaging device shaft 702 has further moved as a result of an additional movement of the proximal repositionable structure. In response, the joints 704 have further moved, but are not able to maintain the target position 710 and the target orientation 712 of the imaging device. In addition, the joints 704 are not able to maintain a partially constrained field of view. Instead, a floating field of view 744 is maintained such that the distal portion of the imaging device moves from the target position 710. In addition, the orientation of the imaging device moves from the target orientation 712. Correspondingly, the image 730 of the first object 720 appears to move to the right relative to the floating field of view 744. Similarly, the image 732 of the second object 722 also appears to move to the right relative to the floating field of view 744.

As shown in FIG. 7D, the imaging device shaft 702 has further moved as a result of an additional movement of the proximal repositionable structure. In response, the joints 704 have further moved, but are not able to maintain the target position 710 and the target orientation 712 of the imaging device. In addition, the joints 704 are not able to maintain a partially constrained field of view. Instead, a floating field of view 744 is maintained such that the distal portion of the imaging device moves farther from the target position 710. In addition, the orientation of the imaging device moves farther from the target orientation 712. Correspondingly, the image 730 of the first object 720 appears to move farther to the right relative to the floating field of view 744. Similarly, the image 732 of the second object 722 also appears to move farther to the right relative to the floating field of view 744. Because the first object 720 is closer to the distal portion of the imaging device relative to the second object 722, the image 730 of the first object 720 appears to move farther to the right relative to the image 732 of the second object 722. In addition, the divergence between the image 730 of the first object 720 and the image 732 of the second object 722 is greater in the floating field of view 746 of FIG. 7D relative to the floating field of view 744 of FIG. 7C. The motion of the joints 704 to maintain the floating field of view corresponds to the remedial action in lieu of the alternate second commanded motion to move the second distal repositionable structure and/or the imaging device.

Referring back to process 322, in some examples, the remedial action includes generating a request to the operator to select between maintaining a fixed field of view or maintaining a floating field of view when the defined geometric relationship between the first geometric feature and the second geometric feature can no longer be maintained due to a commanded motion. In some examples, the control module allows the operator to override the constraint and allow the commanded motion when the defined geometric relationship can no longer be maintained at the fixed location relative to the workspace due to a commanded motion. At a process 324, the control module performs the remedial action. The method 300 then Returns to process 302, described above to handle other commanded motions of the instrument.

As discussed above and further emphasized here, FIGS. 3-7D are merely examples which should not unduly limit the scope of the claims. Many variations, alternatives, and modifications are possible. In some embodiments, the control module generates haptic feedback to help guide the operator 298 when preforming the processes of method 300. In some examples, the control module generates a short duration haptic feedback, such as a brief pulse, when commencing or exiting a state of maintaining a partially constrained field of view and/or maintaining a partially constrained field of view at infinity. In some examples, when maintaining a partially constrained field of view, the control module generates haptic resistance proportional to a difference between: (1) a position and orientation of the distal portion of the imaging device when maintaining a partially constrained field of view begins; and (2) a current position and/or orientation of the distal portion of the imaging device. In some examples, upon transitioning to maintaining a fixed field of view or maintaining a floating field of view, the control module generates haptic feedback consistent with maintaining a fixed field of view or maintaining a floating field of view, respectively.

In some embodiments, and as discussed above the first geometric feature and/or the second geometric feature can be other than point, and can be a line, a plane, and/or the like. In some examples for geometric features, the control module determines two separate fixed locations in the workspace based on any one or more of the techniques described herein. For example, the control module can determine the two fixed locations based on the location of the distal portions of any two instruments introduced to the workspace. The control module then determines a fixed line in the workspace that connects the two fixed locations. The control module determines a line in the field of view where the portion of the workspace that lies along at the fixed line in the workspace is visible in the field of view of the imaging device. The control module maps the 2D line in the field of view to the 3D fixed line within the workspace. In some examples, the control module can determine the geometric features based on two lines in the workspace set at different depths from the imaging device, where the two lines would intersect if projected onto a plane orthogonal to a direction of view of the imaging device.

Some examples of control units, such as the control unit 140 of FIG. 1 can include non-transient, tangible, machine-readable media that include executable code that when executed by a processor system (e.g., the processor system 150 of FIG. 1) can cause the processor system to perform the processes of method 300. Some common forms of machine-readable media that can include the processes of method 300 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted system comprising:

a proximal repositionable structure;

a first distal repositionable structure physically coupled to the proximal repositionable structure; and a processor system communicatively coupled to the proximal repositionable structure, and the first distal repositionable structure;

wherein the processor system is configured to:

determine a first commanded motion of the proximal repositionable structure;

determine a second commanded motion for one or more joints, the one or more joints selected from the group consisting of: joints of the first distal repositionable structure and an imaging device supported by the first distal repositionable structure, wherein when the second commanded motion is performed in conjunction with the first commanded motion, a field of view of the imaging device is maintained relative to a workspace;

determine whether driving the one or more joints in accordance with the second commanded motion would cause the first distal repositionable structure or the imaging device to violate a first constraint; and in response to a determination that driving the one or more joints in accordance with the second commanded motion would cause the first distal repositionable structure or the imaging device to violate the first constraint:

determine an alternate second commanded motion for the one or more joints to maintain a defined geometric relationship between a first geometric feature and a second geometric feature, the first geometric feature fixed relative to the imaging device, and the second geometric feature fixed relative to the workspace, drive the proximal repositionable structure in accordance with the first commanded motion, and drive the one or more joints in accordance with the alternate second commanded motion.

2. The computer-assisted system of claim 1, wherein: to determine whether driving the one or more joints in accordance with the second commanded motion would cause the first distal repositionable structure or the imaging device to violate the first constraint, the processor system is configured to:

determine whether driving the one or more joints in accordance with the second commanded motion would cause a first joint of the one or more joints to violate a physical constraint, the first constraint comprising the physical constraint; or determine whether driving the one or more joints in accordance with the second commanded motion would cause a second joint of the one or more joints to violate a motion constraint, the first constraint comprising the motion constraint; or determine whether driving the one or more joints in accordance with the second commanded motion would cause a distal portion of the imaging device to enter a keep-out zone, wherein the first constraint comprises the keep-out zone.

3. The computer-assisted system of claim 1, wherein:

the first commanded motion of the proximal repositionable structure is determined to move an instrument supported by a second distal repositionable structure, the second distal repositionable structure physically coupled to the proximal repositionable structure and communicatively coupled to the processor system; or the first commanded motion of the proximal repositionable structure is determined based on an operator command to move the instrument, the operator command received by an input system of the computer-assisted system.

4. The computer-assisted system of claim 1, wherein the processor system is further configured to:

determine the second geometric feature based on a location, at a time prior to driving the proximal repositionable structure in response to the first commanded motion, of a distal portion of an instrument supported by a second distal repositionable structure, the second distal repositionable structure physically coupled to the proximal repositionable structure and communicatively coupled to the processor system; or determine the second geometric feature based on locations, at the time prior to driving the proximal repositionable structure in response to the first commanded motion, of distal portions of a plurality of instruments supported by the computer-assisted system.

5. The computer-assisted system of claim 1, wherein:

the second geometric feature comprises a reference location; or the second geometric feature is located along an axis defined relative to a field of view of the imaging device; or the second geometric feature is a point located along an optical axis of the imaging device and at a specified distance from a distal portion of the imaging device.

6. The computer-assisted system of claim 1, wherein:

the defined geometric relationship comprises an intersection of the first geometric feature with the second geometric feature.

7. The computer-assisted system of claim 1, wherein the processor system is further configured to: locate the second geometric feature at a specified distance from a distal portion of the imaging device.

8. The computer-assisted system of claim 7, wherein the processor system is further configured to determine the specified distance based on at least one parameter selected from the group consisting of:

a focal distance of the imaging device;

a depth of an object in the workspace;

locations of an instrument supported by the computer-assisted system;

locations of a plurality of instruments supported by the computer-assisted system; and a type of procedure being performed with the computer-assisted system.

9. The computer-assisted system of claim 1, wherein the processor system is further configured to: locate the second geometric feature at an infinite distance from a distal portion of the imaging device.

10. The computer-assisted system of claim 1, wherein the processor system is further configured to: determine the defined geometric relationship relative to the workspace based on a location of at least one viewable feature in the field of view of the imaging device.

11. The computer-assisted system of claim 1, wherein the processor system is further configured to:

determine a third commanded motion of the proximal repositionable structure;

determine a fourth commanded motion for the one or more joints, wherein when the fourth commanded motion is performed in conjunction with the third commanded motion, the field of view of the imaging device is maintained relative to the workspace;

determine whether driving the one or more joints in accordance with the fourth commanded motion would cause the first distal repositionable structure or the imaging device to violate a second constraint; and in response to a determination that driving the one or more joints in accordance with the fourth commanded motion would cause the first distal repositionable structure or the imaging device to violate the second constraint:

drive the proximal repositionable structure in accordance with the third commanded motion.

12. The computer-assisted system of claim 1, wherein the processor system is further configured to:

determine a third commanded motion of the proximal repositionable structure;

determine a fourth commanded motion for the one or more joints, wherein when the fourth commanded motion is performed in conjunction with the third commanded motion, the field of view of the imaging device is maintained relative to the workspace;

determine whether driving the one or more joints in accordance with the fourth commanded motion would cause the first distal repositionable structure or the imaging device to violate a second constraint; and in response to a determination that driving the one or more joints in accordance with the fourth commanded motion would cause the first distal repositionable structure or the imaging device to violate the second constraint:

determine an alternate fourth commanded motion for the one or more joints to maintain the defined geometric relationship between the first geometric feature and the second geometric feature, and in response to a determination that driving the one or more joints in accordance with the alternate fourth commanded motion would not cause the first distal repositionable structure or the imaging device to violate a third constraint, allow driving of the proximal repositionable structure in accordance with the third commanded motion; and in response to a determination that driving the one or more joints in accordance with the alternate fourth commanded motion would cause the first distal repositionable structure or the imaging device to violate the third constraint, disallow driving of the proximal repositionable structure in accordance with the third commanded motion.

13. A method comprising:

determining, by a processor system comprising one or more processors, a first commanded motion of a proximal repositionable structure;

determining, by the processor system, a second commanded motion for one or more joints, the one or more joints selected from the group consisting of: joints of a first distal repositionable structure and an imaging device, the first distal repositionable structure being physically coupled to the proximal repositionable structure and the imaging device being supported by the first distal repositionable structure, wherein when the second commanded motion is performed in conjunction with the first commanded motion, a field of view of the imaging device is maintained relative to a workspace;

determining, by the processor system, whether driving the one or more joints in accordance with the second commanded motion would cause the first distal repositionable structure or the imaging device to violate a first constraint; and in response to a determination that driving the one or more joints in accordance with the second commanded motion would cause the first distal repositionable structure or the imaging device to violate the first constraint:

determining, by the processor system, an alternate second commanded motion for the one or more joints to maintain a defined geometric relationship between a first geometric feature and a second geometric feature, the first geometric feature fixed relative to the imaging device, and the second geometric feature fixed relative to the workspace, driving, by the processor system, the proximal repositionable structure in accordance with the first commanded motion, and driving, by the processor system, the one or more joints in accordance with the alternate second commanded motion.

14. The method of claim 13, wherein determining whether driving the one or more joints in accordance with the second commanded motion would cause the first distal repositionable structure or the imaging device to violate the first constraint comprises:

determining, by the processor system, whether driving the one or more joints in accordance with the second commanded motion would cause a first joint of the one or more joints to violate a physical constraint, the first constraint comprising the physical constraint; or determining, by the processor system, whether driving the one or more joints in accordance with the second commanded motion would cause the first joint to violate a motion constraint, the first constraint comprising the motion constraint; or determining, by the processor system, whether driving the one or more joints in accordance with the second commanded motion would cause a distal portion of the imaging device to enter a keep-out zone, the first constraint comprising the keep-out zone.

15. The method of claim 13, wherein:

the first commanded motion of the proximal repositionable structure is determined to move an instrument supported by a second distal repositionable structure that is physically coupled to the proximal repositionable structure and communicatively coupled to the processor system; or the first commanded motion of the proximal repositionable structure is determined based on an operator command received by an input system to move the instrument, wherein the input system is configured to be manipulated by an operator.

16. The method of claim 13, further comprising:

determining, by the processor system, the second geometric feature based on a location, at a time prior to driving the proximal repositionable structure in response to the first commanded motion, of a distal portion of an instrument supported by a second distal repositionable structure, the second distal repositionable structure physically coupled to the proximal repositionable structure and communicatively coupled to the processor system; or determining, by the processor system, the second geometric feature based on locations, at a time prior to driving the proximal repositionable structure in response to the first commanded motion, of distal portions of a plurality of instruments supported by a computer-assisted system that includes the processor system.

17. The method of claim 13, wherein:

the second geometric feature comprises a reference location; or the second geometric feature is located along an axis defined relative to a field of view of the imaging device; or the second geometric feature is a point located along an optical axis of the imaging device and a specified distance from a distal portion of the imaging device.

18. The method of claim 13, wherein:

the defined geometric relationship comprises an intersection of the first geometric feature with the second geometric feature.

19. The method of claim 13, further comprising: locating, by the processor system, the second geometric feature at an infinite distance from a distal portion of the imaging device.

20. The method of claim 13, further comprising: determining, by the processor system, the defined geometric relationship relative to the workspace based on a location of at least one viewable feature in the field of view of the imaging device.

21. One or more non-transitory machine-readable media comprising a plurality of machine-readable instructions which when executed by a processor system associated with a computer-assisted system are adapted to cause the processor system to perform a method comprising determining a first commanded motion of a proximal repositionable structure;

determining a second commanded motion for one or more joints, the one or more joints selected from the group consisting of: joints of a first distal repositionable structure and an imaging device, the first distal repositionable structure being physically coupled to the proximal repositionable structure and the imaging device being supported by the first distal repositionable structure, wherein when the second commanded motion is performed in conjunction with the first commanded motion, a field of view of the imaging device is maintained relative to a workspace;

determining whether driving the one or more joints in accordance with the second commanded motion would cause the first distal repositionable structure or the imaging device to violate a first constraint; and in response to a determination that driving the one or more joints in accordance with the second commanded motion would cause the first distal repositionable structure or the imaging device to violate the first constraint:

determining an alternate second commanded motion for the one or more joints to maintain a defined geometric relationship between a first geometric feature and a second geometric feature, the first geometric feature fixed relative to the imaging device, and the second geometric feature fixed relative to the workspace, driving the proximal repositionable structure in accordance with the first commanded motion, and driving the one or more joints in accordance with the alternate second commanded motion.

22. The one or more non-transitory machine-readable media of claim 21, wherein:

the second geometric feature comprises a reference location; or the second geometric feature is located along an axis defined relative to a field of view of the imaging device; or the second geometric feature is a point located along an optical axis of the imaging device and a specified distance from a distal portion of the imaging device; or the defined geometric relationship comprises an intersection of the first geometric feature with the second geometric feature.

* * * * *